US012266436B2

(12) United States Patent
Breton et al.

(10) Patent No.: US 12,266,436 B2
(45) Date of Patent: *Apr. 1, 2025

(54) METHOD AND SYSTEM FOR THE SAFETY, ANALYSIS AND SUPERVISION OF INSULIN PUMP ACTION AND OTHER MODES OF INSULIN DELIVERY IN DIABETES

(71) Applicant: UNIVERSITY OF VIRGINIA PATENT FOUNDATION, Charlottesville, VA (US)

(72) Inventors: Marc D. Breton, Charlottesville, VA (US); Stephen D. Patek, Charlottesville, VA (US); Boris P. Kovatchev, Charlottesville, VA (US); Colleen H. Karvetski, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 852 days.

This patent is subject to a terminal disclaimer.

(21) Appl. No.: 17/339,153

(22) Filed: Jun. 4, 2021

(65) Prior Publication Data

US 2021/0313036 A1 Oct. 7, 2021

Related U.S. Application Data

(63) Continuation of application No. 13/634,040, filed as application No. PCT/US2011/028163 on Mar. 11, 2011, now Pat. No. 11,069,434.

(60) Provisional application No. 61/312,916, filed on Mar. 11, 2010.

(51) Int. Cl.
*G16H 20/17* (2018.01)
*A61M 5/168* (2006.01)
*G01N 33/74* (2006.01)

(52) U.S. Cl.
CPC ........ *G16H 20/17* (2018.01); *A61M 5/16836* (2013.01); *A61M 5/1684* (2013.01); *G01N 33/74* (2013.01); *G01N 2333/62* (2013.01); *G01N 2800/042* (2013.01)

(58) Field of Classification Search
CPC . A61B 5/14532; A61B 5/4839; A61B 5/7275; A61B 5/746; A61B 5/4866; A61B 5/72; A61M 2230/201; A61M 5/14244; A61M 2205/52; A61M 2005/14208; A61M 2205/18; A61M 2205/35; G16H 20/17; G16H 50/20; G16H 50/30; G16H 10/60; G16H 50/50; G16H 20/10; G16H 40/40; G16H 40/60; G16H 70/20; A61P 3/10; A61K 38/28; A61K 9/0019; C12Q 1/006; C12Q 1/54; G01N 33/66; G01N 33/49; G01N 33/48792; G01N 27/3274; G01N 2800/042; G01N 2333/62; G16B 40/00; G16B 40/10; G16B 5/00
See application file for complete search history.

(56) References Cited

U.S. PATENT DOCUMENTS

| | | | |
|---|---|---|---|
| 6,024,090 A | 2/2000 | Gonda et al. | |
| 6,923,763 B1* | 8/2005 | Kovatchev | G16H 20/17 |
| | | | 128/920 |
| 9,398,869 B2* | 7/2016 | Kovatchev | A61M 1/36 |
| 10,169,544 B2* | 1/2019 | Breton | G16Z 99/00 |
| 10,332,615 B2* | 6/2019 | Kovatchev | A61B 5/7267 |
| 10,420,489 B2* | 9/2019 | Kovatchev | A61B 5/7275 |
| 10,431,342 B2* | 10/2019 | Kovatchev | G16Z 99/00 |
| 10,438,700 B2* | 10/2019 | Ortiz | C12Q 1/54 |
| 10,565,170 B2* | 2/2020 | Walling | G01N 33/66 |
| 10,610,154 B2* | 4/2020 | Kovatchev | G16H 20/10 |
| 10,881,334 B2* | 1/2021 | Facchinetti | A61B 5/14532 |
| 10,925,536 B2* | 2/2021 | Kovatchev | G16H 50/70 |
| 11,024,429 B2* | 6/2021 | Patek | A61B 5/4812 |
| 11,069,434 B2* | 7/2021 | Breton | G16H 50/30 |
| 11,289,201 B2* | 3/2022 | Breton | G16H 50/30 |
| 11,311,665 B2* | 4/2022 | Breton | A61B 5/486 |
| 11,567,062 B2* | 1/2023 | Kovatchev | G01N 33/49 |
| 2006/0094947 A1 | 5/2006 | Kovatchev et al. | |
| 2008/0199894 A1 | 8/2008 | Galasso | |
| 2008/0314395 A1 | 12/2008 | Kovatchev et al. | |
| 2009/0164239 A1 | 6/2009 | Hayter et al. | |
| 2009/0234213 A1 | 9/2009 | Hayes et al. | |
| 2009/0281519 A1 | 11/2009 | Rao et al. | |
| 2011/0029269 A1* | 2/2011 | Hayter | A61M 5/1723 |
| | | | 702/104 |
| 2013/0116649 A1 | 5/2013 | Breton et al. | |

FOREIGN PATENT DOCUMENTS

EP 2545185 A1 1/2013
WO 2011112974 A1 9/2011

OTHER PUBLICATIONS

Dassau et al. Implications of meal library and meal detection to glycemic control of type 1 diabetes mellitus through MPC control. Proceedings of the 17th world congress; the international federation of automatic control; Seoul, Korea, 2008, p. 4228-4233. (Year: 2008).*

Kovatchev et al. Control to range for diabetes: functionality and modular architecture. Journal of Diabetes Science and Technology vol. 3, issue 5, 2009, p. 1058-1065. (Year: 2009).*

The extended European Search Report issued on Aug. 1, 2022, by the European Patent Office in corresponding European Application No. 21214510.6. (10 pages).

(Continued)

*Primary Examiner* — Mary K Zeman
(74) *Attorney, Agent, or Firm* — Buchanan Ingersoll & Rooney, PC

(57) ABSTRACT

An insulin delivery supervisor (IDS) with a safety analysis and supervision function that can reside between the insulin request and the insulin delivery and can intercept any excessive insulin requests before the insulin was delivered. The IDS can be implemented in any system based on insulin pump or pen and will work with either SMBG or CGM modes of blood glucose monitoring.

20 Claims, 19 Drawing Sheets

(56) References Cited

OTHER PUBLICATIONS

Office Action dated Dec. 13, 2018, issued by the Canadian Intellectual Property Office in Canadian Patent Application No. 2,792,758.
Office Action issued on Sep. 25, 2019, by the Canadian Patent Office in corresponding Canadian Patent Application No. 2,792,758 (3 pages).
Andreassen, et al., "A probabilistic approach to glucose prediction and insulin dose adjustment: description of metabolic model and pilot evaluation study", Computer methods and programs in Biomedicine, 1994, vol. 41, pp. 153-165, pp. 153-165.
Kovatchev, et al., "Control to Range for Diabetes: Functionality and Modular Architecture", Journal of Diabetes Science and Technology, vol. 3, Issue 5, Sep. 2009, pp. 1058-1065.
Zisser, et al., "Bolus calculator: a Review of Four Smart Insulin Pumps", Diabetes Technology and Therapeutics, 2008, vol. 10, No. 6, pp. 441-447.

\* cited by examiner

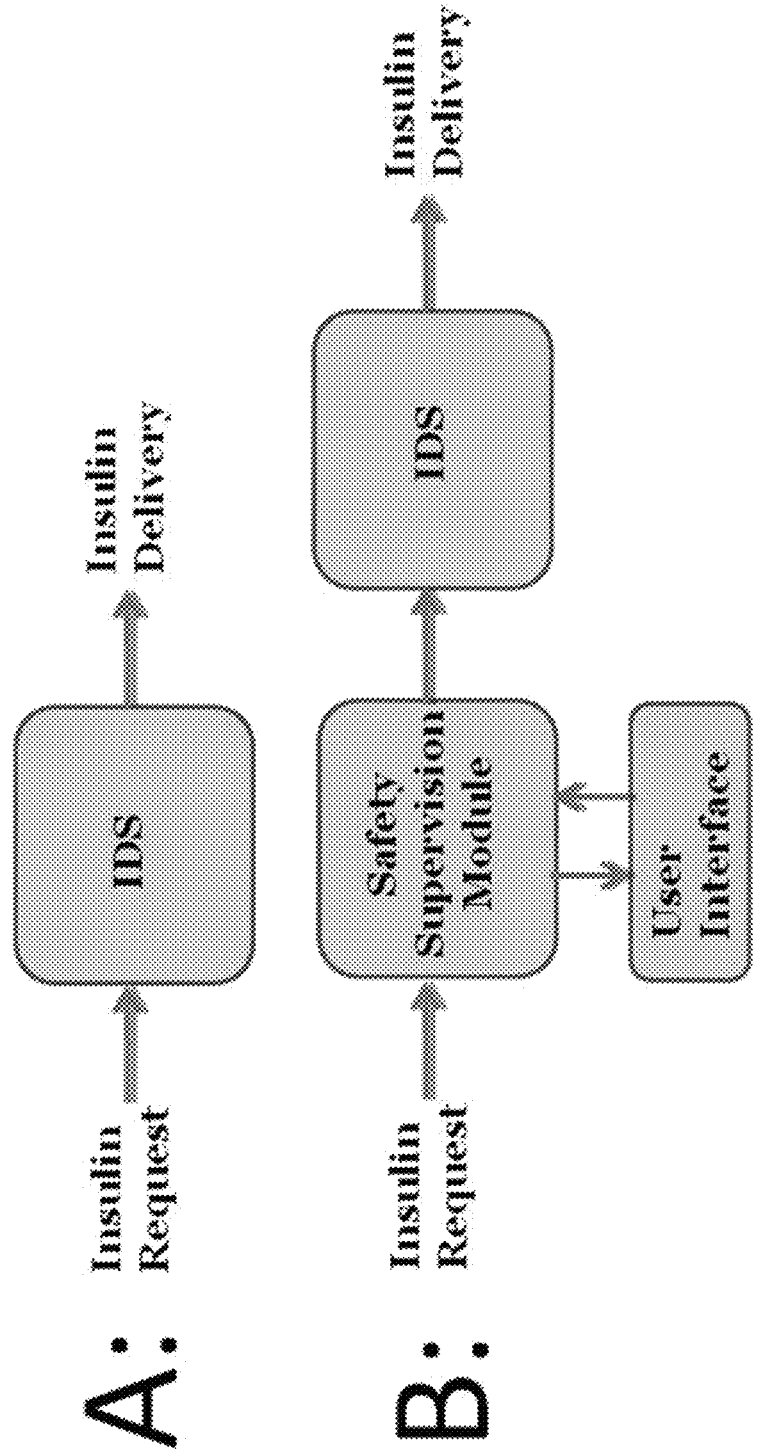
Figure 1: Panel A: Traditional insulin mechanism action: insulin request is followed by immediate insulin delivery.
Panel B: Supervised insulin mechanism action: insulin requests are evaluated by the IDS and any excessive insulin is delivered only after confirmation by the user.

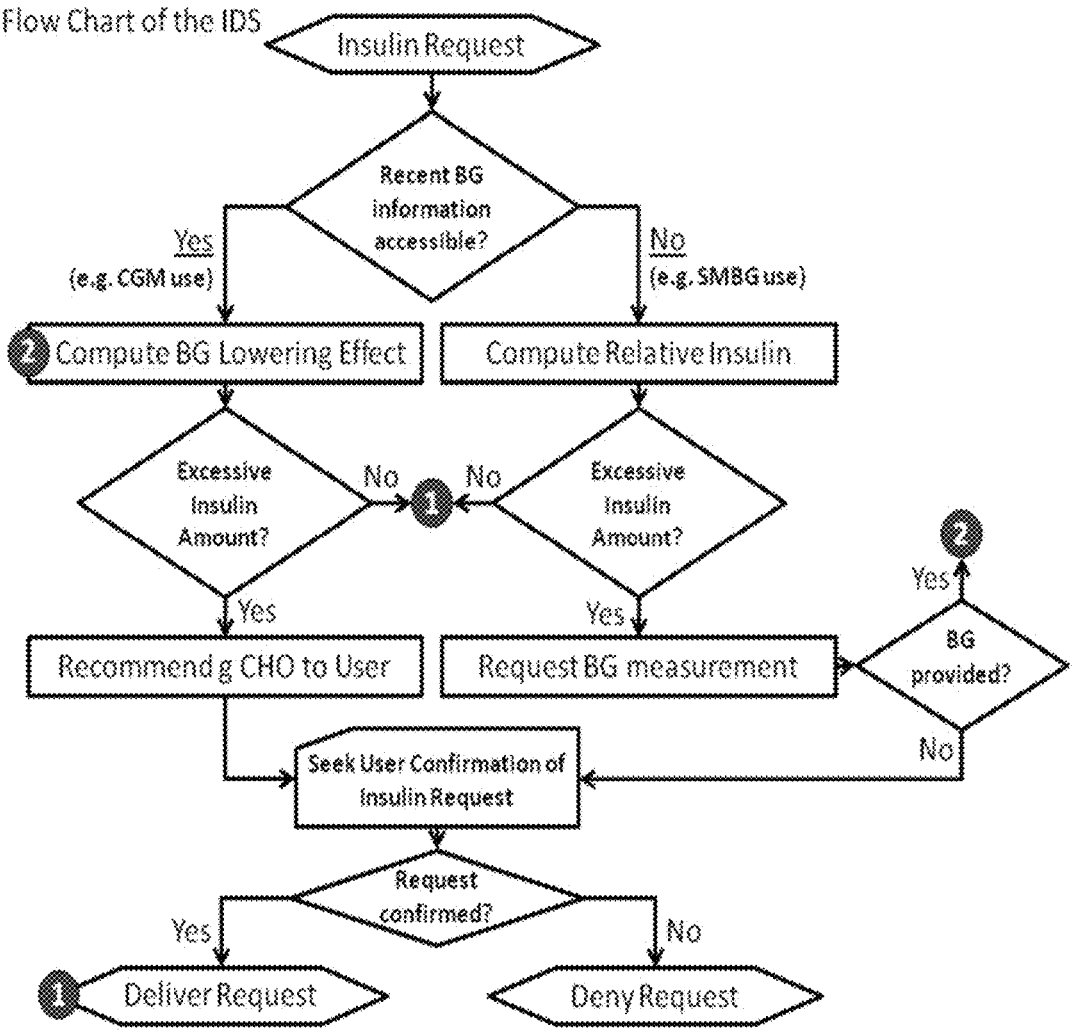

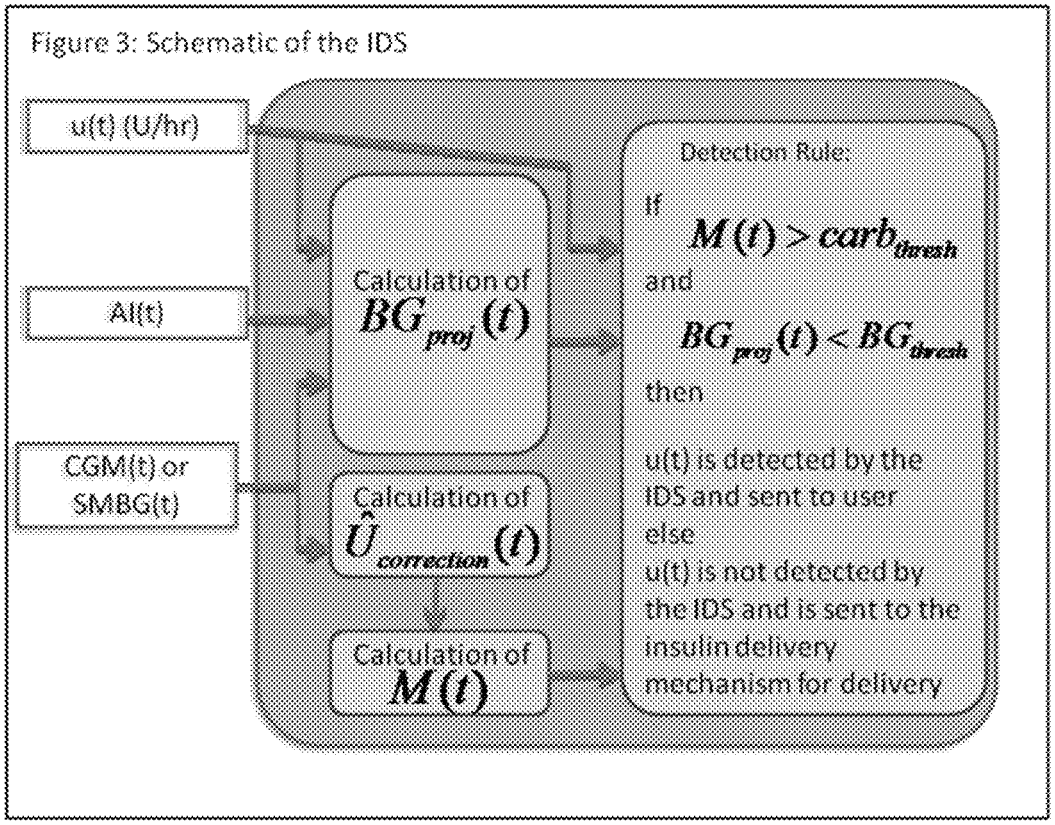

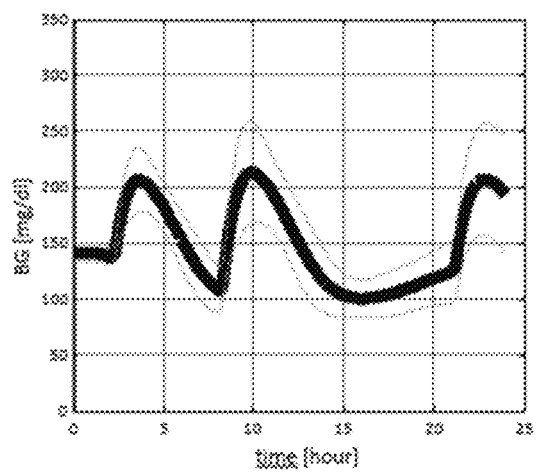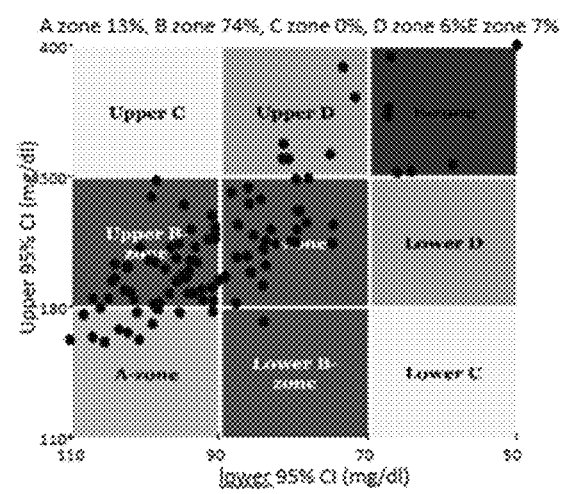
FIGURE 9
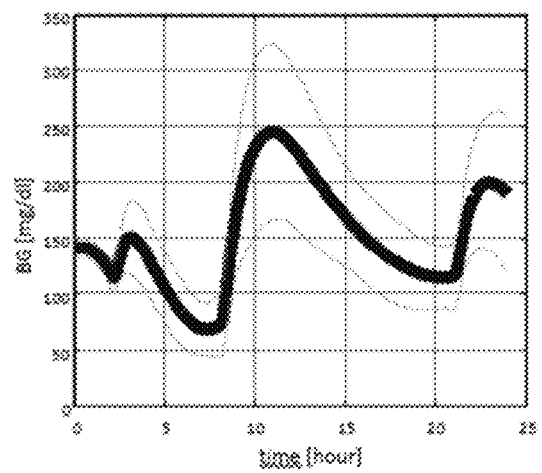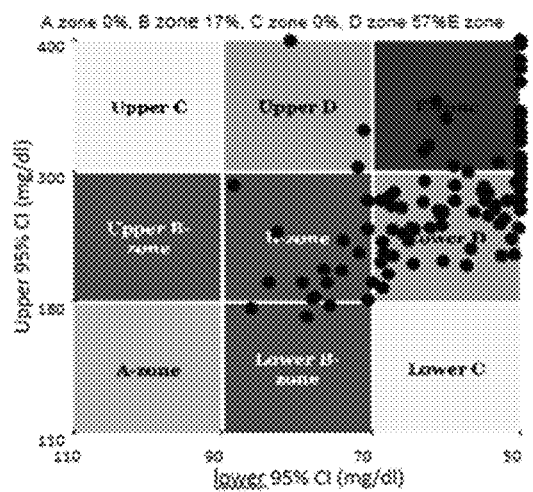
FIGURE 10

METHOD AND SYSTEM FOR THE SAFETY, ANALYSIS AND SUPERVISION OF INSULIN PUMP ACTION AND OTHER MODES OF INSULIN DELIVERY IN DIABETES

CROSS-REFERENCE TO RELATED APPLICATIONS AND CLAIM FOR PRIORITY

The present patent application is a continuation application of U.S. patent application Ser. No. 13/634,040 (now patented as U.S. Pat. No. 11,069,434), filed on Nov. 21, 2012, which is a U.S. national stage application under 35 U.S.C. § 371 for International Patent Application No. PCT/US2011/028163 (now expired), filed on Mar. 11, 2011, which claims priority to U.S. provisional patent application No. 61/312,916, filed on Mar. 11, 2010, the entire contents of each being incorporated by reference.

FIELD

The invention relates to insulin delivery mechanisms and more specifically to insulin delivery mechanisms with safety functions.

BACKGROUND

Hypoglycemia is common in type 1 diabetes (T1DM) [1] and becomes more prevalent in type 2 diabetes (T2DM) with treatment intensification [2]. Hypoglycemia-associated autonomic failure (HAAF) is well documented in T1DM [3,4,5] and is observed in intensively treated T2DM as well [6]. Even state-of-the-art therapies are imperfect and may trigger acute lowering of BG levels, potentially leading to severe hypoglycemia (SH), defined as severe neuroglycopenia resulting in unconsciousness or stupor that precludes self-treatment [1]. SH may cause cognitive dysfunction, coma, or sudden death [1,5]. Consequently, hypoglycemia has been identified as the primary barrier to diabetes management [3].

Insulin Pump and Pen therapy is becoming increasingly prevalent in T1DM and is recommended as means for improvement of glycemic control in T2DM as well. The delivery of insulin by the insulin pump or pen is determined by blood glucose readings that are traditionally obtained by self-monitoring (SMBG) or, more recently, by continuous glucose monitoring (CGM). As a result, all existing safety and hypoglycemia-prevention methods base their decisions on the signals generated by these two types of devices, i.e. either SMBG or CGM data are used to detect, predict, alarm about, and possibly prevent, hypoglycemia [7,8]. An aspect of an embodiment of the present invention employs, for the first time, the requests for insulin delivery as a primary signal for hypoglycemia safety monitoring.

BRIEF SUMMARY

Insulin pump and other delivery mechanisms that include the insulin pen, therapy is becoming increasingly prevalent in the treatment of T1DM. The delivery of insulin by the insulin pump or pen is determined by blood glucose readings that are traditionally obtained by self-monitoring (SMBG) and, more recently, by continuous glucose monitoring (CGM). We introduce a method for using the information from the insulin pump or pen to improve the safety of the insulin therapy by monitoring basal rate, detecting pre-meal insulin boluses, and informing the user of excessive insulin recommendations.

Insulin pump or pen data refers either to (1) commands from the user (in a designated therapy) or controller (in open- or closed-loop control) or (2) feedback from the pump or pen regarding delivered insulin (regardless of the type of control employed). In the proposed method (and related system), insulin pump or pen data is sent to the insulin delivery supervisor prior to being sent to the insulin delivery mechanism. This intermediary step in between insulin request and insulin delivery action allows the opportunity to alert the user of "excessive" insulin request amounts, i.e. those insulin amounts that will result in hypoglycemia if "additional action" is not taken at the time that the insulin amount is delivered. We define "additional action" as any action that can counteract the glucose-lowering effects of insulin; these actions include, but are not limited to, carbohydrate consumption and glucagon injection. In the case where the IDS detects pre-meal boluses, the action taken with insulin delivery is carbohydrate consumption. FIG. 2 presents a flow chart of the IDS action and FIG. 3 provides a schematic of the IDS, using notation explained in Section 6 of this document.

An aspect of an embodiment of the present invention provides, for the first time, the ability to focus on, for example, the signal from the insulin delivery mechanism (pump or pen) as a primary source of information for the safety analysis of insulin delivery in diabetes. Traditionally, the insulin intended for delivery are pre-programmed in the insulin delivery mechanism and are executed at a specific time or upon specific request from the user without further pre-processing, i.e. there are no safety actions taken between insulin request and insulin delivery. An aspect of an embodiment of the present invention provides the insertion of a safety analysis and supervision function—the Insulin Delivery Supervisor (IDS) that will reside between the insulin request and the insulin delivery and will intercept any excessive insulin requests before the insulin is delivered (FIG. 1).

In such situations, the IDS will issue appropriate messages to the pump or pen user and will ask for confirmation of the excessive insulin amount. A second function of the IDS will be the detection of any pre-meal insulin boluses, i.e. significant amounts of insulin that are typically requested prior to meals, but are not justified by hyperglycemic blood glucose levels. The IDS can be implemented in any system based on insulin pump or pen and will work with either SMBG or CGM modes of blood glucose monitoring.

BRIEF DESCRIPTION OF THE DRAWINGS

FIG. 1 shows block diagrams of a traditional insulin mechanism action and a supervised insulin mechanism action;

FIG. 2 shows a Flow chart of an IDS according to one embodiment of the present invention;

FIG. 3 shows a schematic of an IDS according to one embodiment of the present invention;

FIGS. 9 and 10 show test results of an in silico evaluation of the safety supervision system used in conjunction with a PID controller with miscalculated basal rates involving 100 simulated adult subjects in 24-hour closed-loop.

DETAILED DESCRIPTION OF EXEMPLARY EMBODIMENTS OF THE INVENTION

Figure 4A:
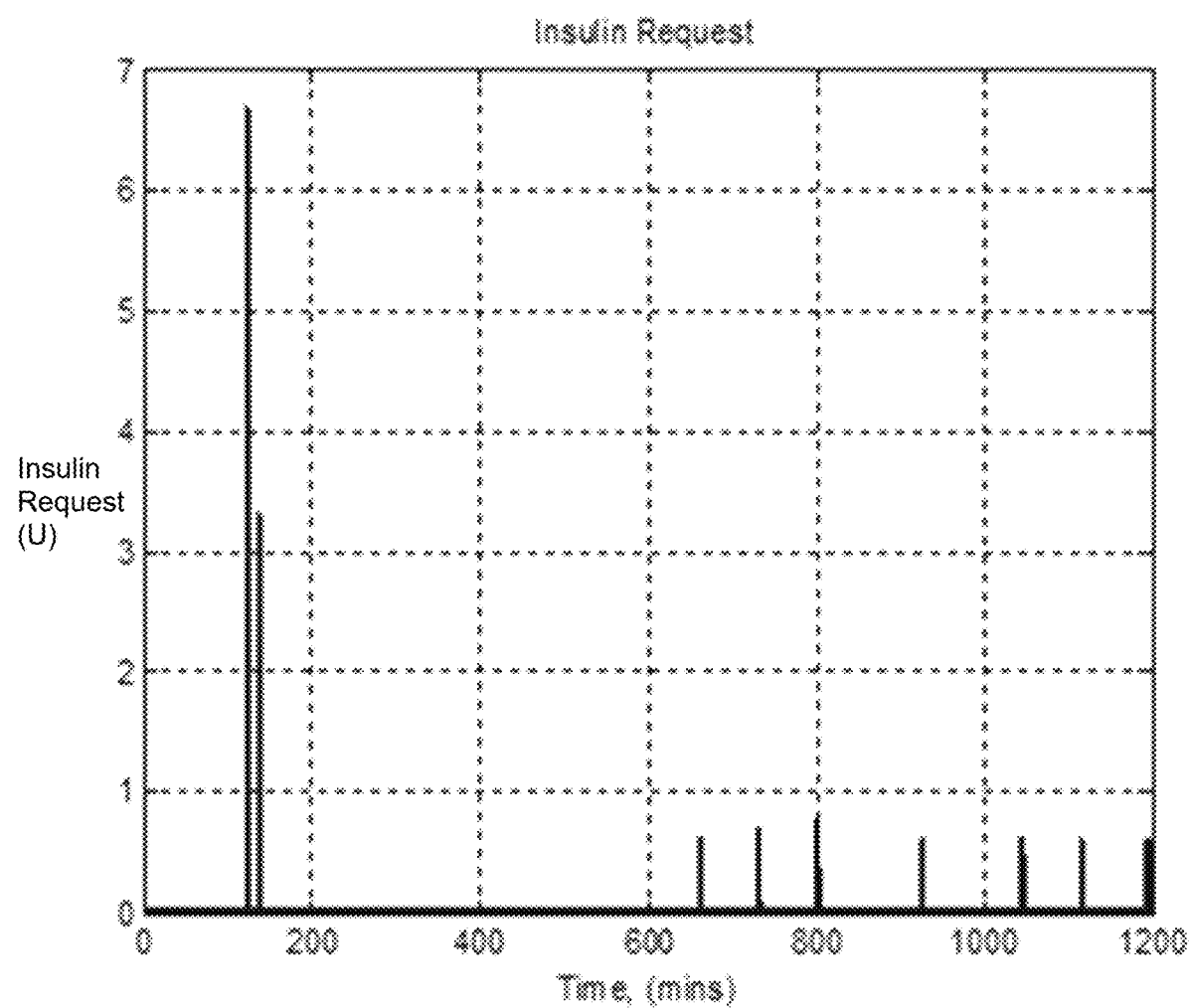
FIGS. 4A-4C provide a graphical Representation of Method 1.2.

For the purpose of this disclosure, we have divided this section into two subsections: (6.1) the description of various embodiments of the invention as it is implemented with an insulin pump, and (6.2) the description of various embodiments of the invention as it is implemented with an insulin pen. The IDS presented here can be implemented using SMBG or CGM modes of blood glucose monitoring, either using model-based methods or a designated-therapy approach, for example, but not limited thereto, that relies on the patient's knowledge of his/her carbohydrate ratio and correction factor (both are typically well known by patients with diabetes but can vary depending on external factors, such as meal composition or physical activity). The IDS resides between the request for insulin delivery done by the user or automatically and the insulin delivery mechanism and uses the request for insulin delivery as a primary signal for safety analysis. The description of the IDS for different modes of implementation is structured as follows:

Section 6.1 presents the IDS as it is implemented in conjunction with an insulin pump.

Section 6.1.1 presents the IDS for the case when SMBG blood glucose monitoring is used.

Section 6.1.1.1 presents the IDS for the case when SMBG is used together with a designated therapy approach.

Section 6.1.1.2 presents the IDS for the case when SMBG is used together with a model-based approach.

Section 6.1.2 presents the IDS for the case when CGM blood glucose monitoring is used.

Section 6.1.2.1 presents the IDS for the case when CGM is used together with a designated therapy approach.

Section 6.1.2.2 presents the IDS for the case when CGM is used together with a model-based approach.

Section 6.2 presents the IDS as it is implemented in conjunction with an insulin pen.

Section 6.2.1 presents the IDS for the case when SMBG blood glucose monitoring is used.

Section 6.2.1.1 presents the IDS for the case when SMBG is used together with a designated therapy approach.

Section 6.2.1.2 presents the IDS for the case when SMBG is used together with a model-based approach.

Section 6.2.2 presents the IDS for the case when CGM blood glucose monitoring is used.

Section 6.2.2.1 presents the IDS for the case when CGM is used together with a designated therapy approach.

Section 6.2.2.2 presents the IDS for the case when CGM is used together with a model-based approach.

A non-limiting, exemplary distinguishing aspect of the system, method and computer program product (compared to other methods of preventing hypoglycemia) is its use of information from the insulin delivery mechanism to alert the user of excessive insulin recommendations from the delivery mechanism and to detect pre-meal insulin bolus recommendations from the insulin delivery mechanism which are not justified by hyperglycemic blood glucose concentrations.

Section 6.1 IDS Implemented with an Insulin Pump as the Mode of Insulin Delivery

Section 6.1.1 IDS Used in Conjunction with SMBG

In this section, we describe the operation of the insulin delivery supervisor in the case where the user employs self-monitoring of blood glucose measurements.

Section 6.1.1.1 IDS Used in Conjunction with SMBG and a Designated Therapy

Approach: Method 1.1 Recent SMBG Available

In this case, a designated therapy approach for detection of excessive or pre-meal boluses is applied.

Let us define the request to the insulin pump at time t by u(t) (U/hr) and BR(t) (U/hr) as the basal rate of the subject at time t. The goal of the method presented here is to assess if u(t) is an excessive amount of insulin or a pre-meal bolus, at which time an alert is sent to the user prior to the delivery of u(t), giving the user notification of the injection as well as the opportunity to modify or cancel it. One important component of this algorithm is the consideration of active insulin (AI), defined as insulin that has been delivered but has yet to act. An assessment of AI can be obtained from standard methods [11]. We refer to active insulin implemented in conjunction with an insulin pump as $AI_{pump}(t)$. We distinguish this from $AI_{pen}(t)$, which will be defined in Section 6.2. It is important to explain that, in computing $AI_{pump}(t)$, the active insulin refers to any insulin that has been injected that has not been detected by the IDS as an excessive or pre-meal bolus. For insulin that is detected by the IDS as excessive or pre-meal insulin, we assume that the user has taken the action recommended by the IDS and that this action "compensates" for the injected insulin.

Let SMBG(t) (mg/dl) represent the most recent self-monitoring BG assessment at time t. We recognize that it is possible that this measurement was taken some amount of time prior to time t, although most individuals who do perform self-monitoring will do so prior to the delivery of large amounts of insulin given in conjunction with meals or to control for glucose concentrations above the target value. (In Method 1.2 we consider a method for the case in which no recent SMBG measurement is available.)

(1) Step 1 of our method is to compute a projected blood glucose concentration conditional on the injection u(t) being delivered in full. Given SMBG(t) and $AI_{pump}(t)$, $BG_{proj}(t)$ (m g/dl):

$$BG_{proj}(t) = SMBG(t) - \left[\frac{u(t) - BR(t)}{k} + AI_{pump}(t)\right] \cdot CF \quad (1.1)$$

where 60/k is the control update interval of insulin data (in minutes), $AI_{pump}(t)$ is the assessment of active insulin at time t and CF is the self-assessed correction factor of the patient, given in mg/dlU. $BG_{proj}(t)$ allows us to determine the effect that injecting u(t) will have on the blood glucose concentration of the patient, while accounting for active insulin and the current state of the patient (the SMBG value).

(2) Step 2 of the method is to make an assessment of the amount of carbohydrates (g) that would be required to maintain a target blood glucose concentration, given the insulin recommendation u(t). To do so, we first generate an estimate of the amount of insulin that would be necessary to account for a positive deviation from the target glucose value, $BG_{target}$, given the most recent assessment of blood glucose concentration, SMBG(t). We refer to this value as $\hat{U}_{correction}(t)$:

$$\hat{U}_{correction}(t) = \frac{SMBG(t) - BG_{target}}{CF} - AI_{pump}(t) \quad (1.2)$$

(3) Step 3 is to compute M(t), the amount of carbohydrates required to maintain $BG_{target}$ conditional on u(t) being delivered in full:

$$M(t) = \max\left\{0, \left[\frac{u(t) - BR(t)}{k} - \hat{U}_{correction}(t)\right] \cdot CR\right\} \quad (1.3)$$

where 60/k is the control update interval of insulin data (in minutes) and CR is the self-assessed carbohydrate ratio (in gCHO/U) of the subject. Note that we only allow for positive values of M(t), as a negative carbohydrate consumption is not realizable. Equations (1.1), (1.2), and (1.3) summarize the computations necessary to assess the recommended insulin injection from the insulin pump, u(t), as being an excessive or pre-meal bolus using the following threshold comparisons:

If $BG_{proj}(t) < BG_{thresh}$ and if $M(t) > carb_{thresh}$, we classify the bolus as an excessive amount that will cause hypoglycemia unless additional action is taken with the delivery of u(t). The values of $BG_{thresh}$ and $carb_{thresh}$ are chosen so as to ensure that the excessive or pre-meal boluses are detected, while allowing other insulin recommendations from the insulin pump pass through the supervisor module undetected. In the event that $BG_{proj}(t) < BG_{thresh}$ and $M(t) > carb_{thresh}$, an alert is sent to the user which states, for example: "This insulin amount is large enough to cause hypoglycemia if additional action is not taken. The IDS recommends M(t)gCHO to be taken with this meal". We may also suggest in this message to the user an amount of insulin (less than the amount requested) that could be delivered while still avoiding hypoglycemia risk. This amount of insulin would be computed using Equation 1.2, where the $BG_{target}$ replaced target is with a low BG threshold that avoids hypoglycemia, for example 80 mg/dl. The output of Equation 1.2, in this form, provides an amount of insulin to the user that can be taken while avoiding hypoglycemia.

The values of $BG_{thresh}$ and $carb_{thresh}$ depend on the embodiment of the IDS. In some embodiments, we may set the value of $BG_{thresh}$ high (e.g. 130 mg/dl) and the value of $carb_{thresh}$ low (e.g. 5 gCHO), so as to ensure that even relatively small insulin requests are sent to the user for approval. Alternatively, setting $BG_{thresh}$ closer to a hypoglycemic threshold (70 mg/dl) and $carb_{thresh}$ to the value of a moderately sized meal (60 gCHO) allows for the IDS to alert the user less frequently. These values may also be set for individual patients depending on their personal preferences regarding alert frequency.

IDS Used in a Designated Therapy Approach: Method 1.2—recent SMBG not available

In some instances, it may be the case that no recent SMBG measurement is available at the time that an insulin request is sent to the IDS. Suppose that there has been no SMBG measurement taken in the past τ minutes, where τ may be, for example, any period of time greater than 30 minutes. We now consider a method for assessing insulin requests that does not rely on the use of any blood glucose measurement data.

This method approximates the carbohydrates required to compensate for the insulin request a time t:

To compute M(t), the amount of carbohydrates required to maintain $BG_{target}$ conditional on u(t) being delivered in full:

$$M(t) = \frac{u(t) - BR(t)}{k} \cdot CR \quad (1.4)$$

where 60/k is the control update interval of insulin data (in minutes) and CR is the self-assessed carbohydrate ratio (in gCHO/U) of the subject. Because Equation (1.4) does not require a measure of BG, the alert sent to the user when an excessive bolus is detected via Method 1.2 will state, "You are requesting a large bolus, which may cause hypoglycemia. Please measure BG before bolus delivery". Obtaining a BG measurement will allow the IDS to make a more accurate evaluation of the safety of the insulin request. With a BG measurement from the user in response to this request, we can proceed to Equations (1.1), (1.2), and (1.3) to provide the user with a carbohydrate recommendation. In the event that the user does not provide a BG measurement, Equation (1.4) gives us a method for assessing insulin requests as being excessive in the sense that delivery of u(t) would require M(t) g carbohydrates to compensate for the insulin delivered. FIG. 2 provides a flow chart for the scenario in Methods 1.1 and 1.2.

Equation (4) can be used to categorize u(t) as being an excessive or pre-meal bolus using the following threshold comparison:

If $M(t) > carb_{thresh}$, then we classify the bolus as an excessive amount that may cause hypoglycemia unless additional action is taken with the delivery of u(t). Because Method 1.2 is less-informed than Method 1.1 presented above, we have the option to set the threshold value of $carb_{thresh}$ more conservatively so as to ensure that excessive insulin requests are detected by the IDS.

Exemplary Embodiment Method 1.2 with $carb_{thresh}=20$ mg/dl, where we assume that no BG measurement is obtained from the user. The results are obtained from the UVA Metabolic Simulator. The controller employed in this illustrative example operates by delivering a continuous basal infusion of insulin, delivering a correction bolus to target a glucose concentration of 150 mg/dl when the blood glucose estimate is greater than 180 mg/dl, and delivering a meal bolus at mealtime computed using the carbohydrate ratio (U/gCHO) of the subject. An option for a "meal supervisory bolus" is also available, where a bolus is delivered 15 minutes following the meal bolus if the meal bolus is deemed not large enough to cover the entire meal.

Figure 4B:
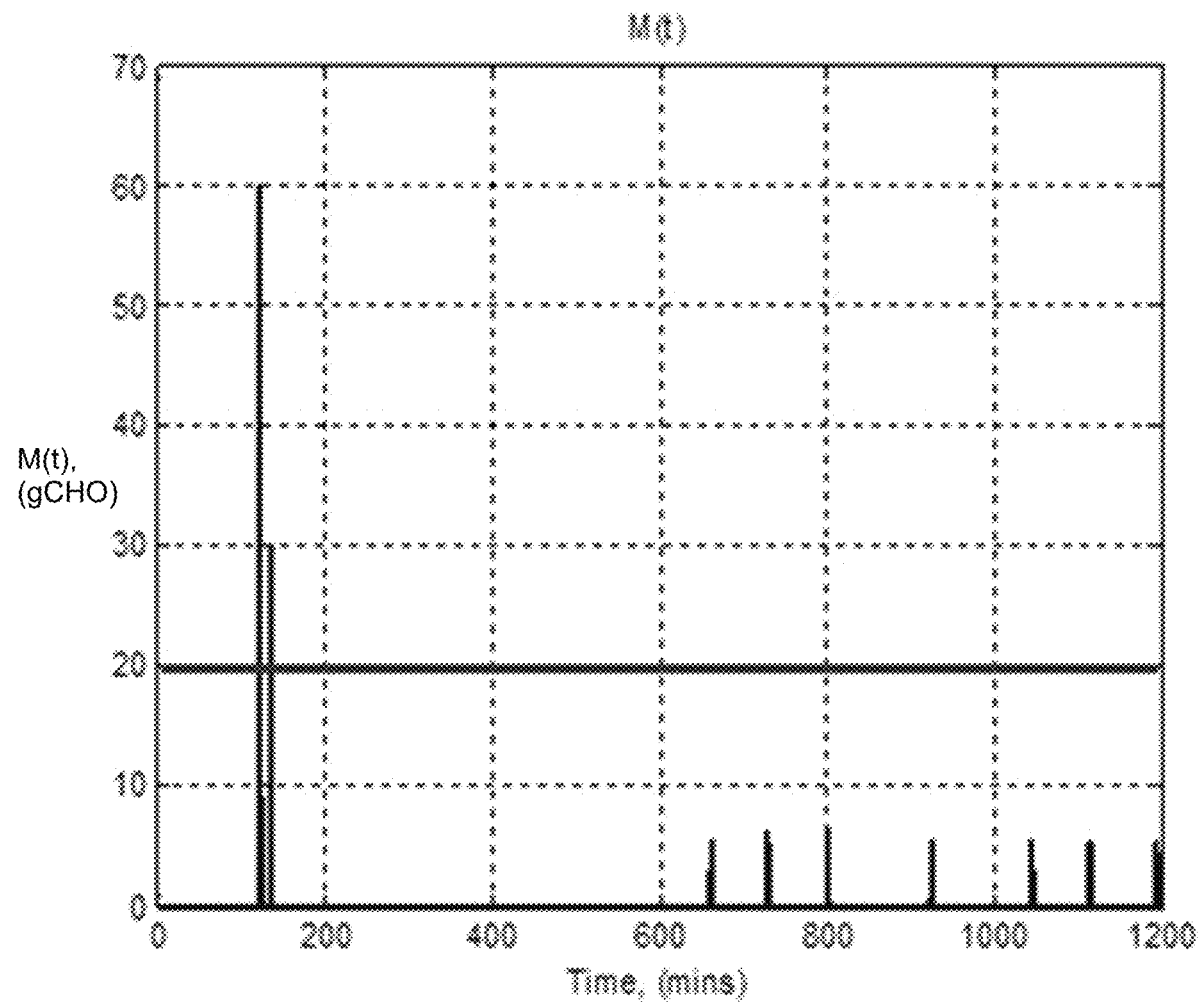
Figure 4C:
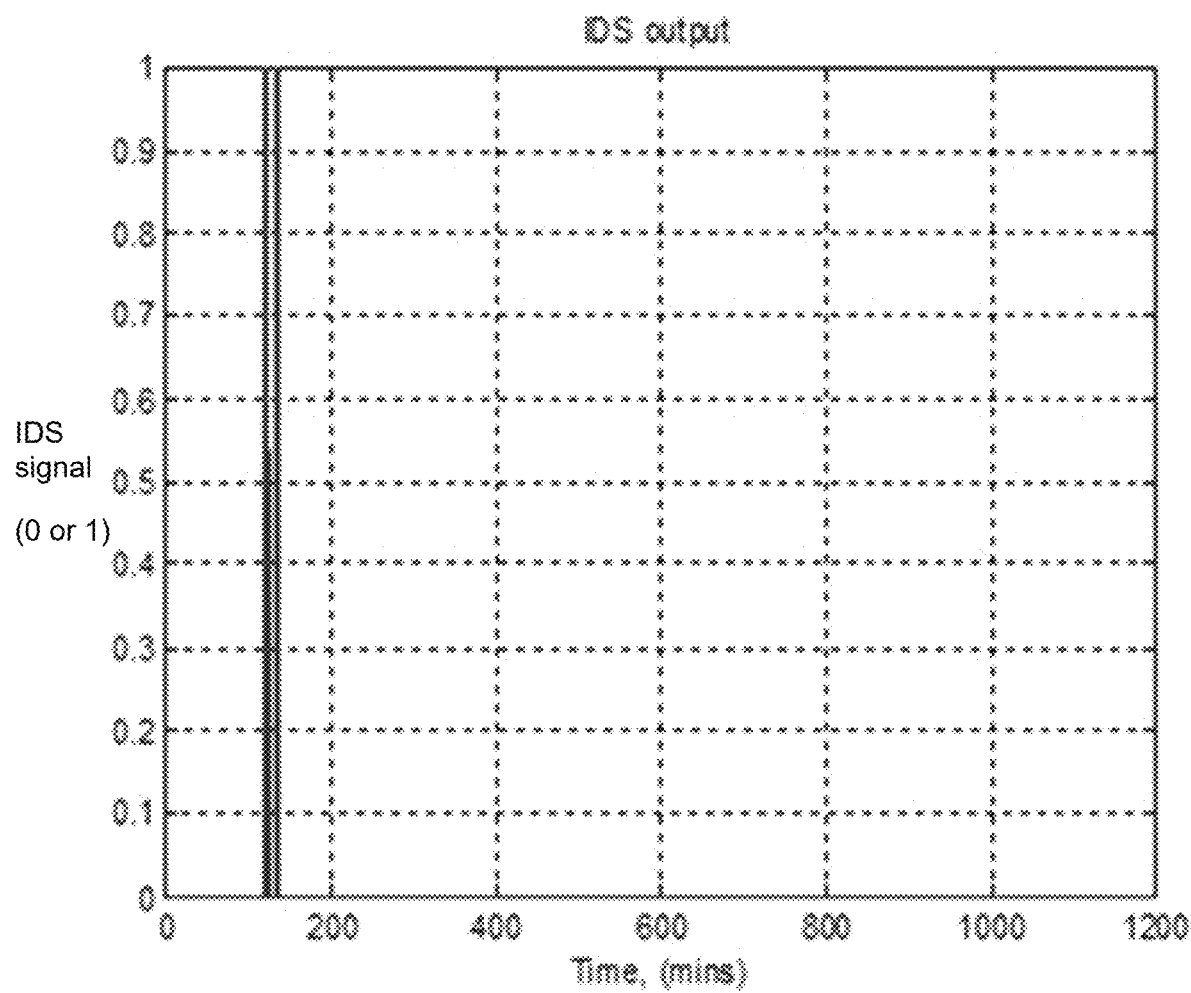

In the scenario demonstrated here for a representative subject, a meal is delivered at hour 2 of the simulation. Following the meal, the basal rate is reduced to ½ the basal rate designed to maintain a blood glucose steady state at 112.5 mg/dl. In this way, the blood glucose concentration of the subject increases, giving the controller an opportunity to request the delivery of a series of correction boluses. The controller is designed to limit the delivery of correction boluses to one correction bolus every 60 minutes. Results indicate that the meal bolus (at time 120 minutes) and the supervisory meal bolus that follows 15 minutes later (at time 135 minutes) are detected, while the small correction boluses pass through the IDS undetected. This is because the correction boluses are assessed as posing no risk of hypoglycemia to the user when delivered with no other action from the user, while the two meal boluses are assessed as large enough to cause hypoglycemia if action (in this case, carbohydrate consumption) is not taken by the user. The results for a representative subject are shown in FIGS. 4A-4C.

Section 6.1.1.2 IDS Used in Conjunction with SMBG and a Model-Based Approach

Method 2

This method (and related system and computer program product) begins by computing a value of $BG_{proj}$, as in Equation (1.1). In this case, $BG_{proj}$ is computed with the use of a metabolic state observer, which in turn (1) requires a model of blood glucose-insulin dynamics and (2) requires knowledge of insulin pump requests. Let x(t) denote a vector of metabolic states associated with the patient, representing, for example, interstitial glucose concentration, plasma glucose concentration, insulin concentrations, contents of the gut, etc. Let $\hat{x}(t)$ denote the estimate of x(t) using all available input data up to time t, based on a linear state space model expressed generically as $$x(t) = Ax(t-1) + Bu_m(t-1) + G\omega(t-1) \tag{1.5}$$

where $u_m(t)$ represents the insulin signal at time t and $\omega(t)$ represents the disturbance process of the model. We note that, while this model provides the opportunity for representing ingested carbohydrates as a model input, the IDS assumes no knowledge of meal information, thus meals are modeled as a disturbance process. Because this method is intended to determine the projected effect of insulin requests on blood glucose concentration when no additional action (e.g. meals) is associated with the insulin delivery, the model assumes no knowledge of meal timing or meal size.

This model-based formulation allows us to assess the projected state of the system given that the insulin request at time t, u(t), is delivered in full. We note again that the index t is a discrete-time index with a sampling period corresponding to the frequency of the insulin data signal.

We compute the projected blood glucose value, $BG_{proj}$, as $$BG_{proj}(t) = C\hat{x}_\tau(t) \tag{1.6}$$

where C is a matrix that relates the metabolic state vector to measured glucose, $\tau$ is a nonnegative integer parameter, and $$\hat{x}_\tau(t) = A^\tau \hat{x}(t) + A(\tau)Bu_m(t) + A(\tau)G\omega(t) \tag{1.7}$$

where $A^\tau$ is the A matrix of the state space model raised to the $\tau$-th power and $$A(\tau) = \begin{cases} 0 & \text{if } \tau = 0 \\ \sum_{s=0}^{\tau-1} & \text{if } \tau > 0 \end{cases} \tag{1.8}$$

In this method of computing $BG_{proj}(t)$, the state space model (A, B, G, C), the state observer giving the estimate $\hat{x}(t)$, and the parameter $\tau$ are all specific to the embodiment of the invention.

The choice of $\tau$ depends upon the embodiment of the system. $\tau=0$ corresponds to assessing the projected blood glucose value based on the best estimate of blood glucose based on all of the data received up to time t. $\tau>0$ corresponds to an assessment of the future projected blood glucose based on a forecast of the state of the system some time period in the future. We note that as $\tau\to\infty$, the model-based method presented in this section converges to a form of the designated therapy approach presented in Section 6.1.1.2.

Exemplary Embodiment—SMBG with a Model-Based Approach: Method 2

Here we present an exemplary embodiment of the IDS using Method 2 of computing projected glucose $BG_{proj}(t)$. We employ a population-average model for glucose-insulin kinetics, as described by the vector difference equation:

$$x(t) = Ax(t-1) + Bu_m(t-1) + G\omega(t-1) \tag{1.9}$$

Where t is a discrete time index with the interval from t to t+1 corresponding to the sampling time of insulin data in real time and 1. $x(t) = (\partial G(t)\ \partial X(t)\ \partial I_{sc1}(t)\ \partial I_{sc2}(t)\ \partial I_p(t)\ \partial G_{sc}(t)\ \partial Q_1(t)\ \partial Q_2(t))^T$ is a vector of state variables referring to:
   a. blood glucose: $\partial G(t) = G(t) - G_{ref}$, where G(t) mg/dl is blood glucose concentration at minute t and $G_{ref} = 112.5$ (mg/dl) is a reference value for BG
   b. remote compartment insulin action: $\partial X(t) = X(t) - X_{ref}$ where X(t) (min$^{-1}$) represents the action of insulin in the "remote" compartment and $X_{ref} = 0$ (min$^{-1}$) is a reference value
   c. interstitial insulin, first compartment: $\partial I_{sc1}(t) = I_{sc1}(t) - I_{sc1,ref}$, where $I_{sc1}(t)$ (mU) is insulin stored in the first of two interstitial compartments and $I_{sc1,ref} = 1.2949 \times 10^3$ (mU) is a reference value
   d. interstitial insulin, second compartment: $\partial I_{sc2}(t) = I_{sc2}(t) - I_{sc2,ref}$, where $I_{sc2}(t)$ (mU) is insulin stored in the first of two interstitial compartments and $I_{sc2,ref} = 1.2949 \times 10^3$ (mU) is a reference value
   e. plasma insulin: $\partial I_p(t) = I_p(t) - I_{p,ref}$, where $I_p(t)$ (mU) is plasma insulin and $I_{p,ref} = 111.2009$ (mU) is a reference value
   f. interstitial glucose concentration: $\partial G_{sc}(t) = G_{sc}(t) - G_{sc,ref}$, where $G_{sc}(t)$ (mg/dl) is the concentration of glucose in interstitial fluids, and $G_{sc,ref}$ 112.5 (mg/dl) is a reference value
   g. gut compartment 1: $\partial Q_1(t) = Q_1(t) - Q_{1,ref}$, where $Q_1(t)$ (mg) is glucose stored in the first of two gut compartments and $Q_{1,ref} = 0$ (mg) is a reference value
   h. gut compartment 2: $\partial Q_2(t) = Q_2(t) - Q_{2,ref}$, where $Q_2(t)$ (mg) is glucose stored in the first of two gut compartments and $Q_{2,ref} = 0$ (mg) is a reference value
2. $u_m(t) = u(t) - BR(t)$ (mU/min) is the insulin differential control signal at time t, where u(t) (mU/min) is the current requested rate of insulin infusion and BR(t) (mU/min) is the patient's normal/average basal rate at time t
3. $\omega(t) = \text{meal}(t) - \text{meal}_{ref}$ (mg/min) is the meal disturbance signal at time t, where meal(t) is the rate of glucose ingestion and $\text{meal}_{ref} = 0$ (mg/min) is a reference meal input value.

4. the state space matrices A, B, and G are $$A = \begin{bmatrix} .9913 & -102.7 & -1.50\times10^{-8} & -2.89\times10^{-6} & -4.1\times10^{-4} & 0 & 2.01\times10^{-6} & 4.30\times10^{-5} \\ 0 & .839 & 5.23\times10^{-10} & 7.44\times10^{-8} & 6.84\times10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times10^{-4} & .0180 & .7882 & 0 & 0 & 0 \\ .0865 & -4.667 & -2.73\times10^{-10} & -6.59\times10^{-8} & -1.26\times10^{-5} & .9131 & 6.00\times10^{-8} & 1.90\times10^{-6} \\ 0 & 0 & 0 & 0 & 0 & 0 & .9083 & 0 \\ 0 & 0 & 0 & 0 & 0 & 0 & .09115 & .9891 \end{bmatrix} \quad (1.10)$$

$$B^T = \begin{bmatrix} -3.05\times10^{-9} & 1.34\times10^{-10} & .9900 & .0100 & 6.50\times10^{-5} & -4.61\times10^{-11} & 0 & 0 \end{bmatrix}$$

$$G^T = \begin{bmatrix} 6.76\times10^{-7} & 0 & 0 & 0 & 0 & 1.52\times10^{-8} & .9534 & 0.0464 \end{bmatrix}$$

Estimates $\hat{x}(t)$ of $x(t)$ are computed based on knowledge of infused insulin $u(t)$ and SMBG measurements $y(t)$ (mg/dl). In the case of SMBG, it is likely that the model will not receive a new SMBG measurement each time the model receives an insulin data sample. To account for this, SMBG measurements, represented by $y(t)$, are held constant between samples. We model the measurement signal as $$y(t) - G_{ref} = Cx(t) + v(t) \quad (1.11)$$

where $v(t)$ (mg/dl) represents SMBG signal noise and the state space matrix C is $$C^T = [1\ 0\ 0\ 0\ 0\ 0\ 0\ 0] \quad (1.12)$$

The metabolic state observer is derived from the state space model for $x(t)$ and $y(t)$ as a Kalman filter, treating the meal disturbance process $\omega(t)$ and the noise process $v(t)$ as zero-mean, white, Gaussian processes with covariances $R = k_1 = 0.01$ and $Q = k_2 = 0.0005$, respectively. (We point out that, even though model disturbances $\omega(t)$ and sensor noise $v(t)$ are not zero-mean, white, Guassian processes in reality, the resulting Kalman filter is still a stable state observer.)

Section 6.1.2 IDS Used in Conjunction with CGM

Here, we describe the IDS for the case where a CGM is used for blood glucose monitoring.

Section 6.1.2.1 IDS Used in Conjunction with CGM and a Designated Therapy

Approach: Method 3

In this case, a designated therapy approach for detection of excessive boluses is applied in conjunction with CGM blood glucose measurement.

Let us define the recommendation from the insulin pump at time t by $u(t)$ (U/hr). The goal of the method presented here is to assess if $u(t)$ is an excessive amount of insulin or a pre-meal bolus, at which time an alert is sent to the user prior to the delivery of $u(t)$, giving the user notification of the injection as well as the opportunity to modify it. One important component of this algorithm is the consideration of active insulin (AI), defined as insulin that has been delivered but has yet to act. AI can be obtained from standard methods [11]. Let $CGM(t)$ (mg/dl) represent the measurement obtained from the continuous glucose monitor at time t. We note that because the CGM measurement signal contains noise, it may be desirable to employ a filter (e.g. a moving average filter) to the CGM measurement signal prior to the calculations that follow in Equations (1.13), (1.14), and (1.15). This filtered CGM is represented by $\overline{CGM}(t)$.

(1) Step 1 of our method is to compute a projected blood glucose concentration conditional on the injection $u(t)$ being delivered in full. Given CGM information and active insulin, $BG_{proj}(t)$ (mg/dl):

$$BG_{proj}(t) = \overline{CGM}(t) - \left[\frac{u(t) - BR(t)}{k} + AI_{pump}(t)\right] \cdot CF \quad (1.13)$$

where 60/k is the control update interval of insulin data (in minutes), $AI_{pump}(t)$ is the assessment of active insulin at time t and CF is the self-assessed correction factor of the patient, given in mg/dlU. $BG_{proj}(t)$ allows us to determine the effect that injecting $u(t)$ will have on the blood glucose concentration of the patient, while accounting for active insulin and the current state of the patient.

(2) Step 2 of the method is to make an assessment of the amount of carbohydrates (g) that would be required to maintain a target blood glucose concentration, given the insulin recommendation $u(t)$. To do so, we first generate an estimate of the amount of insulin that would be necessary to account for a positive deviation from the target glucose value, $BG_{target}$, given the CGM information. We refer to this value as $\hat{U}_{correction}(t)$:

$$\hat{U}_{correction}(t) = \frac{\overline{CGM}(t) - BG_{target}}{CF} - AI_{pump}(t) \quad (1.14)$$

where $BG_{target}$ (mg/dl) is a target glucose concentration.

(3) Step 3 is to compute $M(t)$, the amount of carbohydrates required to maintain $BG_{target}$ conditional on $u(t)$ being delivered in full:

$$M(t) = \max\left\{0, \left[\frac{u(t) - BR(t)}{k} - \hat{U}_{correction}(t)\right] \cdot CR\right\} \quad (1.15)$$

where 60/k is the control update interval of insulin data (in minutes) and CR is the self-assessed carbohydrate ratio (in gCHO/U) of the subject. Equations (1.13), (1.14), and (1.15) summarize the computations necessary to assess the recommended insulin injection from the insulin pump, $u(t)$, as being an excessive or pre-meal bolus using the following threshold comparisons:

If $BG_{proj}(t) \leq BG_{thresh}$ and if $M(t) > carb_{thresh}$, we classify the bolus as an excessive amount that will cause hypoglycemia unless additional action, in the form of carbohydrate consumption or glucagon injection, is taken with the delivery of u(t). The values of $BG_{thresh}$ and $carb_{thresh}$ are chosen so as to ensure that the excessive or pre-meal boluses are detected, while allowing other insulin recommendations from the insulin pump pass through the insulin supervisor module undetected. The values of $BG_{thresh}$ and $carb_{thresh}$ depend on the embodiment of the IDS.

Exemplary Embodiment Method 3 with $BG_{thresh}=120$ mg/dl, $carb_{thresh}=20$ mg/dl, $BG_{target}=112.5$ mg/dl, and $$\overline{CGM}(t) = \frac{1}{10}\sum_{i=0}^{9} CGM(t-i).$$

The results are obtained from the UVA Metabolic Simulator.

The scenario and the controller used to generate insulin requests is the same as that used in the Results presented for Method 1.2. FIGS. 5A-5E shows the detection of excessive or pre-meal boluses for a representative subject.

Section 6.1.2.2 IDS Used in Conjunction with CGM and a Model-Based Approach

Method 4

This method and system begins by computing a value of $BG_{proj}$, as in Equation (1.13). In this case, $BG_{proj}$ is computed with the use of a metabolic state observer, which in turn (1) requires a model of blood glucose-insulin dynamics and (2) requires knowledge of insulin pump requests. Let x(t) denote a vector of metabolic states associated with the patient, representing, for example, interstitial glucose concentration, plasma glucose concentration, insulin concentrations, contents of the gut, etc. Let $\hat{x}(t)$ denote the estimate of x(t) using all available input data up to time t, based on a linear state space model expressed generically as $$x(t)=Ax(t-1)+Bu_m(t-1)+G\omega(t-1) \quad (1.16)$$

where $u_m(t)$ represents the insulin signal at time t and $\omega(t)$ represents the disturbance process of the model. We note that, while this model provides the opportunity for representing ingested carbohydrates as a model input, the IDS assumes no knowledge of meal information, thus meals are modeled as a disturbance process. Because this method is intended to determine the projected effect of insulin requests on blood glucose concentration when no additional action (e.g. meals) is associated with the insulin delivery, the model assumes no knowledge of meal timing or meal size.

This model-based formulation allows us to assess the projected state of the system given that the insulin request at time t, u(t), is delivered in full. We note that the index t is a discrete-time index with a sampling period corresponding to the frequency of the CGM measurement signal.

(1) For step 1 of this method, we compute the projected blood glucose value, $BG_{proj}$, as $$BG_{proj}(t)=C\hat{x}_\tau(t) \quad (1.17)$$

where C is a matrix that relates the metabolic state vector to measured glucose, $\tau$ is a nonnegative integer parameter, and $$\hat{x}_\tau(t)=A^\tau \hat{x}(t)+A(\tau)Bu_m(t)+A(\tau)G\omega(t) \quad (1.18)$$

where $A^\tau$ is the A matrix of the state space model raised to the $\tau$-th power and $$A(\tau) = \begin{cases} 0 & \text{if } \tau = 0 \\ \sum_{s=0}^{\tau-1} & \text{if } \tau > 0 \end{cases} \quad (1.19)$$

In this method of computing $BG_{proj}(t)$, the state space model (A, B, G, C), the state observer giving the estimate $\hat{x}(t)$, and the parameter $\tau$ are all specific to the embodiment of the invention.

The choice of $\tau$ depends upon the embodiment of the system.

Step 2 of the method is to make an assessment of the amount of carbohydrates (g) that would be required to compensate for the insulin request u(t). To do so, we first generate an estimate of the amount of insulin, $\hat{U}_{correction}(t)$, that would be necessary to account for a positive deviation from the target glucose value, $BG_{target}$, given the CGM information. We note that, given the CGM measurement signal contains noise, it may be desirable to employ a filter (e.g. a 10-minute moving average filter) to the CGM measurement signal. This filtered CGM is represented by $\overline{CGM}(t)$ (2) We compute $\hat{U}_{correction}(t)$ as:

$$\hat{U}_{correction}(t) = \frac{\overline{CGM}(t) - BG_{target}}{CF} - AI_{pump}(t) \quad (1.20)$$

where $BG_{target}$ (mg/dl) is a target glucose concentration.

(3) Step 3 is to compute M(t), the amount of carbohydrates required to maintain $BG_{target}$ conditional on u(t) being delivered in full:

$$M(t) = \max\left\{0, \left[\frac{u(t) - BR(t)}{k} - \hat{U}_{correction}(t)\right] \cdot CR\right\} \quad (1.21)$$

where 60/k is the control update interval of insulin data (in minutes) and CR is the self-assessed carbohydrate ratio (in gCHO/U) of the subject. Note that we only allow for positive values of M(t), as a negative carbohydrate consumption is not realizable. Equations (1.17), (1.20), and (1.21) summarize the computations necessary to assess the recommended insulin injection from the insulin pump, u(t), as being an excessive or pre-meal bolus using the following threshold comparisons:

If $BG_{proj}(t)<BG_{thresh}$ and if $M(t)>carb_{thresh}$, we classify the bolus as an excessive amount that will cause hypoglycemia unless additional action, in the form of carbohydrate consumption or glucagon injection, is taken with the delivery of u(t). The values of $BG_{thresh}$ and $carb_{thresh}$ are chosen so as to ensure that the excessive or pre-meal boluses are detected, while allowing other insulin recommendations from the insulin pump pass through the insulin supervisor module undetected. The values of $BG_{thresh}$ and $carb_{thresh}$ depend on the embodiment of the IDS.

Exemplary Embodiment Method 4 with $BG_{thresh}=120$ mg/dl, $carb_{thresh}=20$ mg/dl, $BG_{target}=112.5$ mg/dl, $\tau=45$ minutes.

Here we present an exemplary embodiment of the IDS using Method 4 to compute projected glucose $BG_{proj}(t)$ and detect excessive insulin requests. We employ a population-average model for glucose-insulin kinetics, as described by the vector difference equation:

$$x(t)=Ax(t-1)+Bu_m(t-1)+G\omega(t-1) \quad (1.22)$$

Where t is a discrete time index with the interval from t to t+1 corresponding to one minute of real time and 1. $x(t)=(\partial G(t) \; \partial X(t) \; \partial I_{sc1}(t) \; \partial I_{sc2}(t) \; \partial I_p(t) \; \partial G_{sc}(t) \; \partial Q_1(t) \; \partial Q_2(t))^T$ is a vector of state variables referring to:
   a. blood glucose: $\partial G(t)=G(t)-G_{ref}$, where $G(t)$ mg/dl is blood glucose concentration at minute t and $G_{ref}=112.5$ (mg/dl) is a reference value for BG
   b. remote compartment insulin action: $\partial X(t)=X(t)-X_{ref}$ where $X(t)$ (min$^{-1}$) represents the action of insulin in the "remote" compartment and $X_{ref}=0$ (min$^{-1}$) is a reference value
   c. interstitial insulin, first compartment: $\partial I_{sc1}(t)=I_{sc1}(t)-I_{sc1,ref}$, where $I_{sc1}(t)$ (mU) is insulin stored in the first of two interstitial compartments and $I_{sc1,ref}=1.2949\times10^3$ (mU) is a reference value
   d. interstitial insulin, second compartment: $\partial I_{sc2}(t)=I_{sc2}(t)-I_{sc2,ref}$, where $I_{sc2}(t)$ (mU) is insulin stored in the first of two interstitial compartments and $I_{sc2,ref}=1.2949\times10^3$ (mU) is a reference value
   e. plasma insulin: $\partial I_p(t)=I_p(t)-I_{p,ref}$, where $I_p(t)$ (mU) is plasma insulin and $I_{p,ref}=111.2009$ (mU) is a reference value
   f. interstitial glucose concentration: $\partial G_{sc}(t)=G_{sc}(t)-G_{sc,ref}$, where $G_{sc}(t)$ (mg/dl) is the concentration of glucose in interstitial fluids, and $G_{sc,ref}$ 112.5 (mg/dl) is a reference value
   g. gut compartment 1: $\partial Q_1(t)=Q_1(t)-Q_{1,ref}$, where $Q_1(t)$ (mg) is glucose stored in the first of two gut compartments and $Q_{1,ref}=0$ (mg) is a reference value
   h. gut compartment 2: $\partial Q_2(t)=Q_2(t)-Q_{2,ref}$, where $Q_2(t)$ (mg) is glucose stored in the first of two gut compartments and $Q_{2,ref}=0$ (mg) is a reference value
2. $u_m(t)=u(t)-BR(t)$ (mU/min) is the insulin differential control signal at time t, where $u(t)$ (mU/min) is the current requested rate of insulin infusion and $BR(t)$ (mU/min) is the patient's normal/average basal rate at time t
3. $\omega(t)=\text{meal}(t)-\text{meal}_{ref}$ (mg/min) is the meal disturbance signal at time t, where meal(t) is the rate of glucose ingestion and $\text{meal}_{ref}=0$ (mg/min) is a reference meal input value.
4. the state space matrices A, B, and G are $$A = \begin{bmatrix} .9913 & -102.7 & -1.50\times10^{-8} & -2.89\times10^{-6} & -4.1\times10^{-4} & 0 & 2.01\times10^{-6} & 4.30\times10^{-5} \\ 0 & .839 & 5.23\times10^{-10} & 7.44\times10^{-8} & 6.84\times10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times10^{-4} & .0180 & .7882 & 0 & 0 & 0 \\ .0865 & -4.667 & -2.73\times10^{-10} & -6.59\times10^{-8} & -1.26\times10^{-5} & .9131 & 6.00\times10^{-8} & 1.90\times10^{-6} \\ 0 & 0 & 0 & 0 & 0 & 0 & .9083 & 0 \\ 0 & 0 & 0 & 0 & 0 & 0 & .09115 & .9891 \end{bmatrix} \quad (1.23)$$

$$B^T = [-3.05\times10^{-9} \; 1.34\times10^{-10} \; .9900 \; .0100 \; 6.50\times10^{-5} \; -4.61\times10^{-11} \; 0 \; 0]$$

$$G^T = [6.76\times10^{-7} \; 0 \; 0 \; 0 \; 0 \; 1.52\times10^{-8} \; .9534 \; 0.0464]$$

Estimates $\hat{x}(t)$ of $x(t)$ are computed based on knowledge of infused insulin $u(t)$ and CGM measurements $y(t)$ (mg/dl). We model the measurement signal as $$y(t)-G_{ref}=Cx(t)+v(t) \quad (1.24)$$

where $v(t)$ (mg/dl) represents CGM signal noise and the state space matrix C is $$C^T=[1 \; 0 \; 0 \; 0 \; 0 \; 0 \; 0 \; 0] \quad (1.25)$$

The metabolic state observer is derived from the state space model for $x(t)$ and $y(t)$ as a Kalman filter, treating the meal disturbance process $\omega(t)$ and the noise process $v(t)$ as zero-mean, white, Gaussian processes with covariances $R=k_1=0.01$ and $Q=k_2=0.0005$, respectively. (We point out that, even though model disturbances $\omega(t)$ and sensor noise $v(t)$ are not zero-mean, white, Guassian processes in reality, the resulting Kalman filter is still a stable state observer.)

The scenario and the controller used to generate insulin requests is the same as that used in the Results presented for Method 1.1 and Method 3, where we employ only insulin data to detect the safety of insulin requests. FIGS. 6A-6E show the Detection of excessive or (pre) meal boluses using Method 4 for a representative subject.

Section 6.2 IDS Implemented with an Insulin Pen as the Mode of Insulin Delivery In this section, we present a method (and related system and computer program product) for implementing the IDS in conjunction with an insulin pen mechanism for insulin delivery.

Section 6.2.1 IDS Used in Conjunction with SMBG

In this section, we describe the operation of the insulin delivery supervisor in the case where the user employs self-monitoring of blood glucose measurements. The main distinction between insulin pump and insulin pen delivery mechanisms is that as insulin pump has the opportunity to deliver insulin in two main forms: a continuous steady-state infusion of insulin delivered throughout the day (commonly referred to as basal insulin) and an insulin bolus, delivered at mealtimes or when glucose concentrations are high. In contrast, to mimic bolus-basal insulin delivery, the insulin pen can use insulin in two forms: rapid acting insulin, which begins working within 15-30 minutes from the time of injection and remains as active for 4-6, and intermediate acting insulin, which begins to work approximately 90 minutes after it is injected and remains active for 16 to 24 hours. For delivery with an insulin pen, the two forms of insulin are delivered using an insulin "mix," commonly denoted by the ratio of intermediate to rapid acting insulin (e.g. 70/30 or 50/50). Because of the variability in insulin action times for rapid acting and intermediate acting insulins delivered in conjunction with an insulin pen, the method used in the IDS for detecting of excessive or pre-meal insulin amounts is different than in the case when an insulin pump is used. In particular, the method needs to be initialized with the proportion (p) of intermediate vs. rapid acting insulin in the insulin mix used in the insulin pen.

Section 6.2.1.1 IDS Used in Conjunction with SMBG and a Designated Therapy

Approach: Method 5.1 Recent SMBG Available

In this case, a designated therapy approach for detection of excessive boluses is applied.

Let us define the request to the insulin pen at time t by u(t) (U/hr) and $u_{int}$(t) (U/hr) as the amount of intermediate acting insulin at time t, represented as a proportion of u(t) by:

$$u_{int}(t) = p \cdot u(t) \quad (2.01)$$

where p is the proportion of intermediate acting insulin in the insulin mix used in the insulin pen. In some instances, the insulin used in the insulin pen is 100% intermediate-acting insulin and in this case, p=1. The goal of the method presented here is to assess if u(t) is an excessive amount of insulin or a pre-meal bolus, at which time an alert is sent to the user prior to the delivery of u(t), giving the user notification of the injection as well as the opportunity to modify it. One important component of this algorithm is the consideration of active insulin (AI), defined as insulin that has been delivered but has yet to act. We refer to active insulin implemented in conjunction with an insulin pen as $AI_{pen}$(t). We distinguish this from $AI_{pump}$(t) defined in Section 6.1. Insulin delivered via the insulin pen may have variable action times in the case when an insulin mix, containing both rapid and intermediate acting insulins, is delivered. For example, suppose that the insulin mix being delivered via the insulin pen is 70% intermediate acting and 30% rapid-acting. Then the total active insulin will be computed separately for each type of insulin delivered, denoted by $AI_{pen,intermediate}$ (t) and $AI_{pen,rapid}$ (t), and the sum of these two active insulin components yields a measure of $AI_{pen}$(t). It is important to explain that, in computing $AI_{pen}$(t) the active insulin refers to any insulin that has been injected that has not been detected by the IDS as an excessive or pre-meal bolus. For insulin that is detected by the IDS as excessive or pre-meal insulin, we assume that the user has taken the action recommended by the IDS and that this action "compensates" for the injected insulin.

Let SMBG(t) (mg/dl) represent the most recent self-monitoring BG assessment at time t. We recognize that it is possible that this measurement was taken some amount of time prior to time t, although most individuals who do perform self-monitoring will do so prior to the delivery of large amounts of insulin given in conjunction with meals or to control for glucose concentrations above the target value.

(4) Step 1 of our method is to compute a projected blood glucose concentration conditional on the injection u(t) being delivered in full. Given SMBG(t) and $AI_{pen}$(t), $BG_{proj}$(t) (mg/dl):

$$BG_{proj}(t) = SMBG(t) - \left[\frac{u(t) - u_{int}(t)}{k} + AI_{pen}(t)\right] \cdot CF \quad (2.1)$$

where 60/k is the control update interval of insulin data (in minutes), $u_{int}$(t) is the amount of intermediate acting insulin at time t (a proportion of u(t) which depends on the insulin mix used in the pen, as defined by Equation 2.01), $AI_{pen}$(t) is the assessment of active insulin at time t and CF is the self-assessed correction factor of the patient, given in mg/dlU.

We note that another way of writing Equation 2.1 is $$BG_{proj}(t) = SMBG(t) - \left[\frac{(1-p) \cdot u(t)}{k} + AI_{pen}(t)\right] \cdot CF \quad (2.1.1)$$

where p is the proportion of intermediate acting insulin in the insulin mix used in the insulin pen, so that (1−p)·u(t) gives a measure of the amount of rapid acting insulin requested at time t. This alternative representation of $BG_{proj}$(t) will not be used in the future description, but should provide insight into the derivation of the equation.

$BG_{proj}$(t) allows us to determine the effect that injecting u(t) will have on the blood glucose concentration of the patient, while accounting for active insulin and the current state of the patient (the SMBG value).

(5) Step 2 of the method is to make an assessment of the amount of carbohydrates (g) that would be required to maintain a target blood glucose concentration, given the insulin recommendation u(t). To do so, we first generate an estimate of the amount of insulin that would be necessary to account for a positive deviation from the target glucose value, $BG_{target}$, given the most recent assessment of blood glucose concentration, SMBG(t). We refer to this value as $\hat{U}_{correction}$(t):

$$\hat{U}_{correction}(t) = \frac{SMBG(t) - BG_{target}}{CF} - AI_{pen}(t) \quad (2.2)$$

(6) Step 3 is to compute M(t), the amount of carbohydrates required to maintain $BG_{target}$ conditional on u(t) being delivered in full:

$$M(t) = \max\left\{0, \left[\frac{u(t) - u_{int}(t)}{k} - \hat{U}_{correction}(t)\right] \cdot CR\right\} \quad (2.3)$$

where 60/k is the control update interval of insulin data (in minutes), $u_{int}$(t)(U/hr) is defined by Equation 2.01, and CR is the self-assessed carbohydrate ratio (in gCHO/U) of the subject. Note that we only allow for positive values of M(t), as negative carbohydrate consumption is not realizable. Equations (2.1), (2.2), and (2.3) summarize the computations necessary to assess the recommended insulin injection from the insulin pen, u(t), as being an excessive or pre-meal bolus using the following threshold comparisons:

If $BG_{proj}(t) < BG_{thresh}$ and if $M(t) > carb_{thresh}$, we classify the bolus as an excessive amount that will cause hypoglycemia unless additional action is taken with the delivery of u(t). The values of $BG_{thresh}$ and $carb_{thresh}$ are chosen so as to ensure that the excessive or pre-meal boluses are detected, while allowing other insulin recommendations from the insulin pen pass through the supervisor module undetected. In the event that $BG_{proj}(t) < BG_{thresh}$ and $M(t) > carb_{thresh}$, an alert is sent to the user which states, "This insulin amount is large enough to cause hypoglycemia if additional action is not taken. The IDS recommends M(t) gCHO to be taken with this meal". We may also suggest in this message to the user an amount of insulin (less than the amount requested) that could be delivered while still avoiding hypoglycemia risk. This amount of insulin would be computed using Equation 1.2, where the $BG_{target}$ is replaced with a low BG threshold that avoids hypoglycemia, for example 80 mg/dl.

The output of Equation 1.2, in this form, provides an amount of insulin to the user that can be taken while avoiding hypoglycemia.

The values of $BG_{thresh}$ and $carb_{thresh}$ depend on the embodiment of the IDS. In some embodiments, we may set the value of $BG_{thresh}$ high (e.g. 130 mg/dl) and the value of $carb_{thresh}$ low (e.g. 5 gCHO), so as to ensure that even relatively small insulin requests are sent to the user for approval. Alternatively, setting $BG_{thresh}$ closer to a hypoglycemic threshold (70 mg/dl) and $carb_{thresh}$ to the value of a moderately sized meal (60 gCHO) allows for the IDS to alert the user less frequently. These values may also be set for individual patients depending on their personal preferences regarding alert frequency.

IDS Used in a Designated Therapy Approach: Method 5.2 Recent SMBG not Available In some instances, it may be the case that no recent SMBG measurement is available at the time that an insulin request is sent to the IDS. Suppose that there has been no SMBG measurement taken in the past $\tau$ minutes, where $\tau$ may be, for example, any period of time greater than 30 minutes. We now consider a method for assessing insulin requests that does not rely on the use of any blood glucose measurement data.

This method approximates the carbohydrates required to compensate for the insulin request a time t:

To compute M(t), the amount of carbohydrates required to maintain $BG_{target}$ conditional on u(t) being delivered in full:

$$M(t) = \frac{u(t) - u_{int}(t)}{k} \cdot CR \quad (2.4)$$

where 60/k is the control update interval of insulin data (in minutes), $u_{int}(t)$ is the amount of intermediate acting insulin at time t defined by Equation 2.01, and CR is the self-assessed carbohydrate ratio (in gCHO/U) of the subject. Because Equation (2.4) does not require a measure of BG, the alert sent to the user when an excessive bolus is detected via Method 5.2 will state, for example: "You are requesting a large bolus, which may cause hypoglycemia. Please measure BG before bolus delivery". Request for a BG measurement will allow the IDS to make a more accurate evaluation of the safety of the insulin request. With a BG measurement from the user in response to this request, we can proceed to Equations (2.1), (2.2), and (2.3) to provide the user with a carbohydrate recommendation. In the event that the user does not provide a BG measurement, Equation (2.4) gives us a method for assessing insulin requests as being excessive in the sense that delivery of u(t) would require M(t)g carbohydrates to compensate for the insulin delivered.

Equation (2.4) alone can be used to categorize u(t) as being an excessive or pre-meal bolus using the following threshold comparison:

If $M(t) > carb_{thresh}$, then we classify the bolus as an excessive amount that will cause hypoglycemia unless additional action is taken with the delivery of u(t). Because Method 5.2 is less-informed than Method 5.1 presented above, we have the option to set the threshold value of $carb_{thresh}$ more conservatively so as to ensure that any excessive insulin requests are detected by the IDS.

Section 6.2.1.2 IDS Used in Conjunction with SMBG and a Model-Based Approach

Method 6

This method (and related system and computer program product) begins by computing a value of $BG_{proj}$, as in Equation (2.1). In this case, $BG_{proj}$ is computed with the use of a metabolic state observer, which in turn (1) requires a model of blood glucose-insulin dynamics and (2) requires knowledge of insulin pen requests. Let x(t) denote a vector of metabolic states associated with the patient, representing, for example, interstitial glucose concentration, plasma glucose concentration, insulin concentrations, contents of the gut, etc. Let $\hat{x}(t)$ denote the estimate of x(t) using all available input data up to time t, based on a linear state space model expressed generically as $$x(t) = Ax(t-1) + Bu_p(t-1) + G\omega(t-1) \quad (2.5)$$

where $u_p(t)$ represents the insulin signal at time t and $\omega(t)$ represents the disturbance process of the model. We note that, while this model provides the opportunity for representing ingested carbohydrates as a model input, the IDS assumes no knowledge of meal information, thus meals are modeled as a disturbance process. Because this method is intended to determine the projected effect of insulin requests on blood glucose concentration when no additional action (e.g. meals) is associated with the insulin delivery, the model assumes no knowledge of meal timing or meal size.

This model-based formulation allows us to assess the projected state of the system given that the insulin request at time t, u(t), is delivered in full. We note again that the index t is a discrete-time index with a sampling period corresponding to the frequency of the insulin data signal.

We compute the projected blood glucose value, $BG_{proj}$, as $$BG_{proj}(t) = C\hat{x}_\tau(t) \quad (2.6)$$

where C is a matrix that relates the metabolic state vector to measured glucose, $\tau$ is a nonnegative integer parameter, and $$\hat{x}_\tau(t) = A^\tau \hat{x}(t) + A(\tau) B u_p(t) + A(\tau) G\omega(t) \quad (2.7)$$

where $A^\tau$ is the A matrix of the state space model raised to the $\tau$-th power and $$A(\tau) = \begin{cases} 0 & \text{if } \tau = 0 \\ \sum_{s=0}^{\tau-1} A^s & \text{if } \tau > 0 \end{cases} \quad (2.8)$$

In this method of computing $BG_{proj}(t)$, the state space model (A, B, G, C), the state observer giving the estimate $\hat{x}(t)$, and the parameter z are all specific to the embodiment of the invention.

The choice of $\tau$ depends upon the embodiment of the system. $\tau=0$ corresponds to assessing the projected blood glucose value based on the best estimate of blood glucose based on all of the data received up to time t. $\tau>0$ corresponds to an assessment of the future projected blood glucose based on a forecast of the state of the system some time period in the future. We note that as $\tau \to \infty$, the model-based method presented in this section converges to a form of the designated therapy approach presented in Section 6.2.1.1.

Section 6.2.2 IDS Used in Conjunction with CGM

Here, we describe the IDS for the case where a CGM is used for blood glucose monitoring.

Section 6.2.2.1 IDS Used in Conjunction with CGM and a Designated Therapy

Approach: Method 7

In this case, a designated therapy approach for detection of excessive boluses is applied in conjunction with CGM blood glucose measurement.

Let us define the recommendation from the insulin pen at time t by u(t) (U/hr). The goal of the method presented here is to assess if u(t) is an excessive amount of insulin or a pre-meal bolus, at which time an alert is sent to the user prior to the delivery of u(t), giving the user notification of the injection as well as the opportunity to modify it. One important component of this algorithm is the consideration of active insulin (AI), defined as insulin that has been delivered but has yet to act. Defining active insulin in the case of the insulin pen, $AI_{pen}(t)$, is described in Section 6.2.1.1.

Let CGM(t) (mg/dl) represent the measurement obtained from the continuous glucose monitor at time 1. We note that, given the CGM measurement signal contains noise, it may be desirable to employ a filter (e.g. a moving average filter) to the CGM measurement signal prior to performing the calculations that follow in Equations (2.13), (2.14), and (2.15). This filtering method is specific to the embodiment and is represented by $\overline{CGM}(t)$.

(4) Step 1 of our method is to compute a projected blood glucose concentration conditional on the injection u(t) being delivered in full. Given CGM information and active insulin, $BG_{proj}$ (t)(mg/dl):

$$BG_{proj}(t) = \overline{CGM}(t) - \left[\frac{u(t) - u_{int}(t)}{k} + AI_{pen}(t)\right] \cdot CF \quad (2.13)$$

where 60/k is the control update interval of insulin data (in minutes), $u_{int}(t)$ is the amount of intermediate acting insulin requested at time t defined by Equation 2.01, $AI_{pen}(t)$ is the assessment of active insulin at time t, and CF is the self-assessed correction factor of the patient, given in mg/dlU. $BG_{proj}$ (t) allows us to determine the effect that injecting u(t) will have on the blood glucose concentration of the patient, while accounting for active insulin and the current state of the patient.

(5) Step 2 of the method is to make an assessment of the amount of carbohydrates (g) that would be required to maintain a target blood glucose concentration, given the insulin recommendation u(t). To do so, we first generate an estimate of the amount of insulin that would be necessary to account for a positive deviation from the target glucose value, $BG_{target}$, given the CGM information. We refer to this value as $\hat{U}_{correction}(t)$:

$$\hat{U}_{correction}(t) = \frac{\overline{CGM}(t) - BG_{target}}{CF} - AI_{pen}(t) \quad (2.14)$$

where $BG_{target}$ (mg/dl) is a target glucose concentration.

(6) Step 3 is to compute M(t), the amount of carbohydrates required to maintain $BG_{target}$ conditional on u(t) being delivered in full:

$$M(t) = \max\left\{0, \left[\frac{u(t) - u_{int}(t)}{k} - \hat{U}_{correction}(t)\right] \cdot CR\right\} \quad (2.15)$$

where 60/k is the control update interval of insulin data (in minutes), $u_{int}(t)$ is the amount of intermediate acting insulin requested at time t defined by Equation 2.01, and CR is the self-assessed carbohydrate ratio (in gCHO/U) of the subject. Equations (2.13), (2.14), and (2.15) summarize the computations necessary to assess the recommended insulin injection from the insulin pen, u(t), as being an excessive or pre-meal bolus using the following threshold comparisons:

If $BG_{proj}(t) < BG_{thresh}$ and if $M(t) > carb_{thresh}$, we classify the bolus as an excessive amount that will cause hypoglycemia unless additional action, in the form of carbohydrate consumption or glucagon injection, is taken with the delivery of u(t). The values of $BG_{thresh}$ and $carb_{thresh}$ are chosen so as to ensure that the excessive or pre-meal boluses are detected, while allowing other insulin requests from the insulin pen pass through the insulin supervisor module undetected. The values of $BG_{thresh}$ and $carb_{thresh}$ depend on the embodiment of the IDS.

Section 6.2.2.2 IDS Used in Conjunction with CGM and a Model-Based Approach

Method 8

This method (and related system and computer program product) begins by computing a value of $BG_{proj}$, as in Equation (2.13). In this case, $BG_{proj}$ is computed with the use of a metabolic state observer, which in turn (1) requires a model of blood glucose-insulin dynamics and (2) requires knowledge of insulin pen requests. Let x(t) denote a vector of metabolic states associated with the patient, representing, for example, interstitial glucose concentration, plasma glucose concentration, insulin concentrations, contents of the gut, etc. Let $\hat{x}(t)$ denote the estimate of x(t) using all available input data up to time t, based on a linear state space model expressed generically as $$x(t) = Ax(t-1) + Bu_p(t-1) + G\omega(t-1) \quad (2.16)$$

where $u_p(t)$ represents the insulin signal at time t and $\omega(t)$ represents the disturbance process of the model. We note that, while this model provides the opportunity for representing ingested carbohydrates as a model input, the IDS assumes no knowledge of meal information, thus meals are modeled as a disturbance process. Because this method is intended to determine the projected effect of insulin requests on blood glucose concentration when no additional action (e.g. meals) is associated with the insulin delivery, the model assumes no knowledge of meal timing or meal size.

This model-based formulation allows us to assess the projected state of the system given that the insulin request at time t, u(t), is delivered in full. We note that the index t is a discrete-time index with a sampling period corresponding to the frequency of the CGM measurement signal.

(4) For step 1 of this method, we compute the projected blood glucose value, $BG_{proj}$, as $$BG_{proj}(t) = C\hat{x}_t(t) \quad (2.17)$$

where C is a matrix that relates the metabolic state vector to measured glucose, $\tau$ is a nonnegative integer parameter, and $$\hat{x}_\tau(t) = A^\tau \hat{x}(t) + A(\tau)Bu_p(t) + A(\tau)G\omega(t) \quad (2.18)$$

where $A^\tau$ is the A matrix of the state space model raised to the $\tau$-th power and $$A(\tau) = \begin{cases} 0 & \text{if } \tau = 0 \\ \sum_{s=0}^{\tau-1} A^s & \text{if } \tau > 0 \end{cases} \quad (2.19)$$

In this method of computing $BG_{proj}(t)$, the state space model (A, B, G, C), the state observer giving the estimate $\hat{x}(t)$, and the parameter r are all specific to the embodiment of the invention.

The choice of $\tau$ depends upon the embodiment of the system.

Step 2 of the method is to make an assessment of the amount of carbohydrates (g) that would be required to compensate for the insulin recommendation u(t). To do so, we first generate an estimate of the amount of insulin, $\hat{U}_{correction}(t)$, that would be necessary to account for a positive deviation from the target glucose value, $BG_{target}$, given the CGM information. We note that, given the CGM measurement signal contains noise, it may be desirable to employ a filter (e.g. a 10-minute moving average filter) to the CGM measurement signal. This filtered CGM is represented by $\overline{CGM}(t)$.

(5) We compute $\hat{U}_{correction}(t)$ as:

$$\hat{U}_{correction}(t) = \frac{\overline{CGM}(t) - BG_{target}}{CF} - AI_{pen}(t) \quad (2.20)$$

where $BG_{target}$ (mg/dl) is a target glucose concentration.

(6) Step 3 is to compute M(t), the amount of carbohydrates required to maintain $BG_{target}$ conditional on u(t) being delivered in full:

$$M(t) = \max\left\{0, \left[\frac{u(t) - u_{int}(t)}{k} - \hat{U}_{correction}(t)\right] \cdot CR\right\} \quad (2.21)$$

where 60/k is the control update interval of insulin data (in minutes), $u_{int}(t)$ is the amount of intermediate acting insulin requested at time t defined by Equation 2.01, and CR is the self-assessed carbohydrate ratio (in gCHO/U) of the subject. Note that we only allow for positive values of M(t), as a negative carbohydrate consumption is not realizable. Equations (2.17), (2.20), and (2.21) summarize the computations necessary to assess the recommended insulin injection from the insulin pen, u(t), as being an excessive or pre-meal bolus using the following threshold comparisons:

If $BG_{proj}(t) < BG_{thresh}$ and if $M(t) > carb_{thresh}$, we classify the bolus as an excessive amount that will cause hypoglycemia unless additional action, in the form of carbohydrate consumption or glucagon injection, is taken with the delivery of u(t). The values of $BG_{thresh}$ and $carb_{thresh}$ are chosen so as to ensure that the excessive or pre-meal boluses are detected, while allowing other insulin recommendations from the insulin pen pass through the insulin supervisor module undetected. The values of $BG_{thresh}$ and $carb_{thresh}$ depend on the embodiment of the IDS.

FIG. 1 contains two panels. Panel A shows a traditional insulin mechanism action, wherein an insulin request is followed by immediate insulin delivery. Panel B shows a supervised insulin mechanism action, wherein insulin requests are evaluated by the IDS and any excessive insulin is delivered only after confirmation by the user.

FIG. 2 shows a Flow chart of an IDS according to one embodiment of the present invention. This flow chart indicates the steps taken by the IDS from insulin request to insulin delivery. (1) indicates that the insulin request is sent to the insulin delivery mechanism. (2) indicates that a BG measurement has become available so that the glucose lowering effect of the current insulin request can be computed.

At box 201 an insulin request is received. At box 202 it is determined whether recent blood glucose information is accessible. In this context recent can mean within 48 hours, within 36 hours, within 24 hours, within 12 hours, within 6 hours, within 5 hours, within 4 hours, within 3 hours, within 2 hours, within 1 hour, within 30 minutes, with 15 minutes, within 10 minutes, within 5 minutes, within 4 minutes, within 3 minutes, within 2 minutes, with 1 minutes, or within 30 seconds. If recent blood glucose data is available the control proceeds to box 203 where blood glucose lowering effect is computed. If recent blood glucose data is not available then control can proceed to box 204, where relative insulin can be computed. After the computation described at either of boxes 203 or 204 control can proceed to box 205 or box 206, wherein a determination can be made as to whether the requested amount of insulin is an excessive amount in view of the computation. If the requested amount is not excessive, then control proceeds to (1) where the insulin request is sent to the insulin delivery mechanism. If it is determined at box 205 or box 206 that the insulin amount is not excessive then control can proceed to box 207 or box 208. At box 207 a g CHO recommendation can be displayed or otherwise communicated to the user. The glucose recommendation to the user is the system's estimate based on the size of the requested injection of the number of grams CHO required to avoid hypoglycemia, assuming that the requested insulin bolus is delivered in full (M(t) in the above equations). After the recommendation is displayed control can proceed to box 210. At box 208 a request for a blood glucose measurement can be displayed or otherwise communicated to the user. At box 209, a determination is made as to whether blood glucose measurement is provided. If a blood glucose measurement is provided, then the glucose lowering effect of the current insulin request can be computed, therefore control can revert to box 203. If a blood glucose measurement is not provided, then control can proceed to box 210. At box 210 user confirmation of the insulin request can be sought. If the request, or some modification of the request, is confirmed at box 211, then the insulin request is delivered at box 212. If the request is not confirmed then the insulin request is denied at box 213.

FIG. 3 shows a schematic of an IDS according to one embodiment of the present invention. The following notation is employed in FIG. 3:

AI(t) (U): active insulin u(t) (U/hr): requested injection rate $BG_{proj}(t)$ (mg/dl): projected blood glucose concentration conditional on the injection u(t) being delivered in full (first defined in Equation 1.1).

$\hat{U}_{correction}(t)$ (U): an estimate of the amount of insulin that would be necessary to account for a positive deviation from the target glucose value, $BG_{target}$, given an estimate of blood glucose concentration using SMBG(t) or CGM(t) (first defined in Equation 1.2).

M(t) (gCHO): the amount of carbohydrates required to maintain $BG_{target}$ conditional on u(t) being delivered in full (first defined in Equation 1.3).

$BG_{thresh}$ and $carb_{thresh}$: predefined time-invariant threshold values (mg/dl) and (gCHO) respectively.

FIGS. 4A-4C provides a graphical Representation of Method 1.2. The chart in FIG. 4A shows u(t), insulin injection rate as requested by the controller. The chart in FIG. 4B shows M(t) computed by Equation (1.4) with $carb_{thresh}$=20 g shown in red. The chart in FIG. 4C shows: Detection Signal: "0" indicates that the insulin request passes through the IDS undetected, while "1" indicates that the insulin request is detected by the IDS and user approval is sought.

Figure 5A:
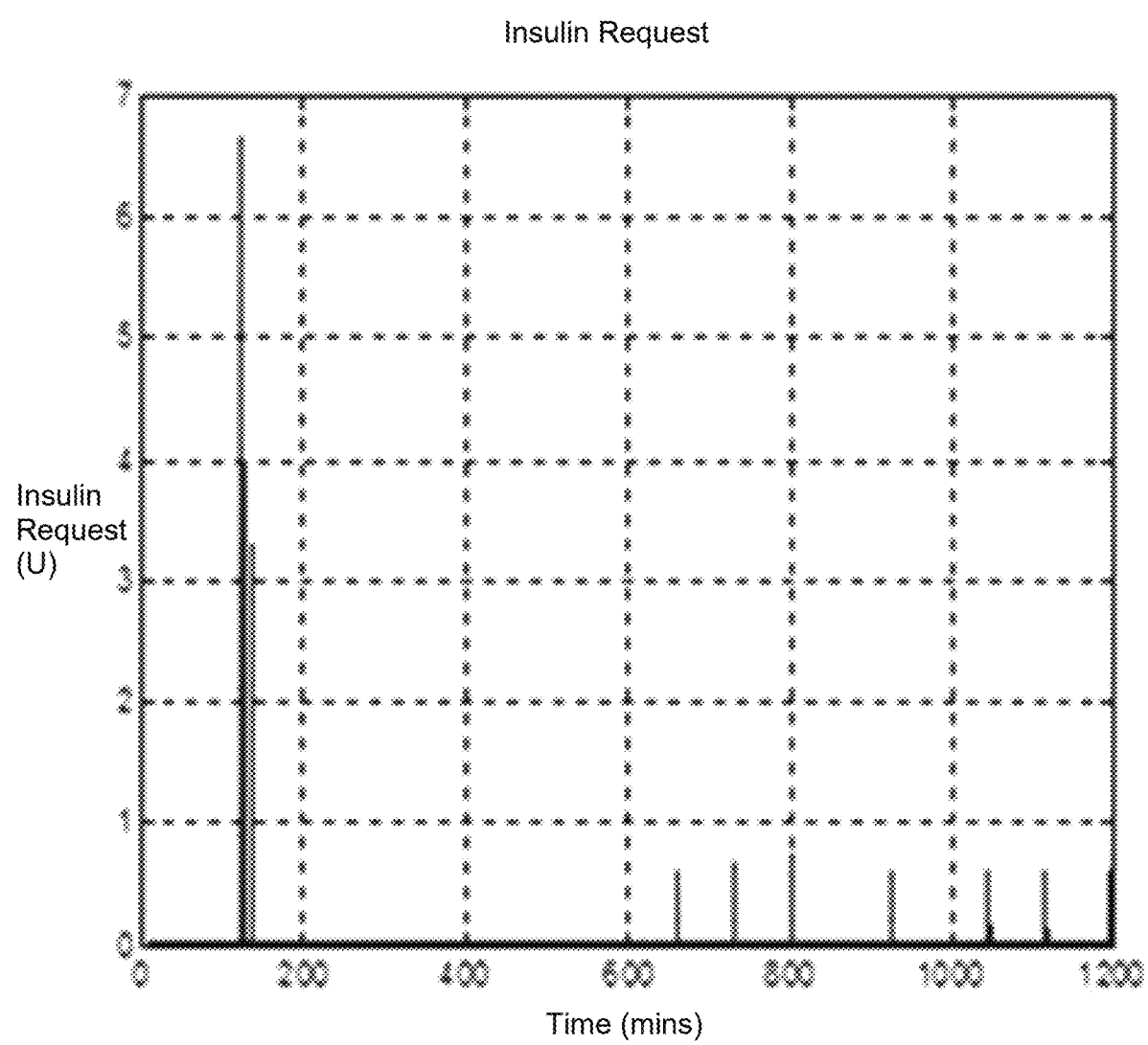
FIGS. 5A-5E show a Graphical Representation of Equations (1.13), (1.14), and (1.15) and the resulting detection signal for Method 3.
Figure 5B:
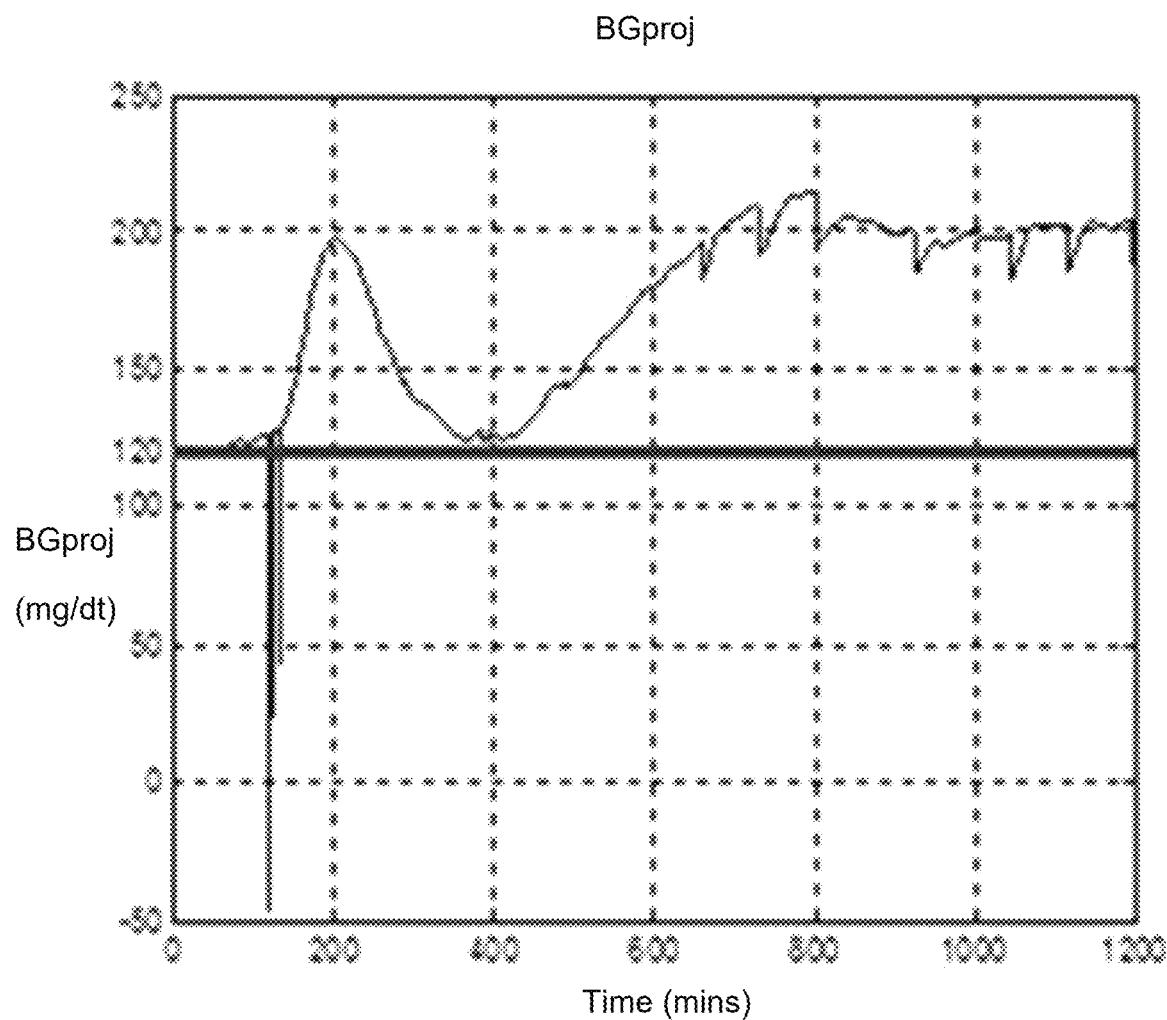
Figure 5C:
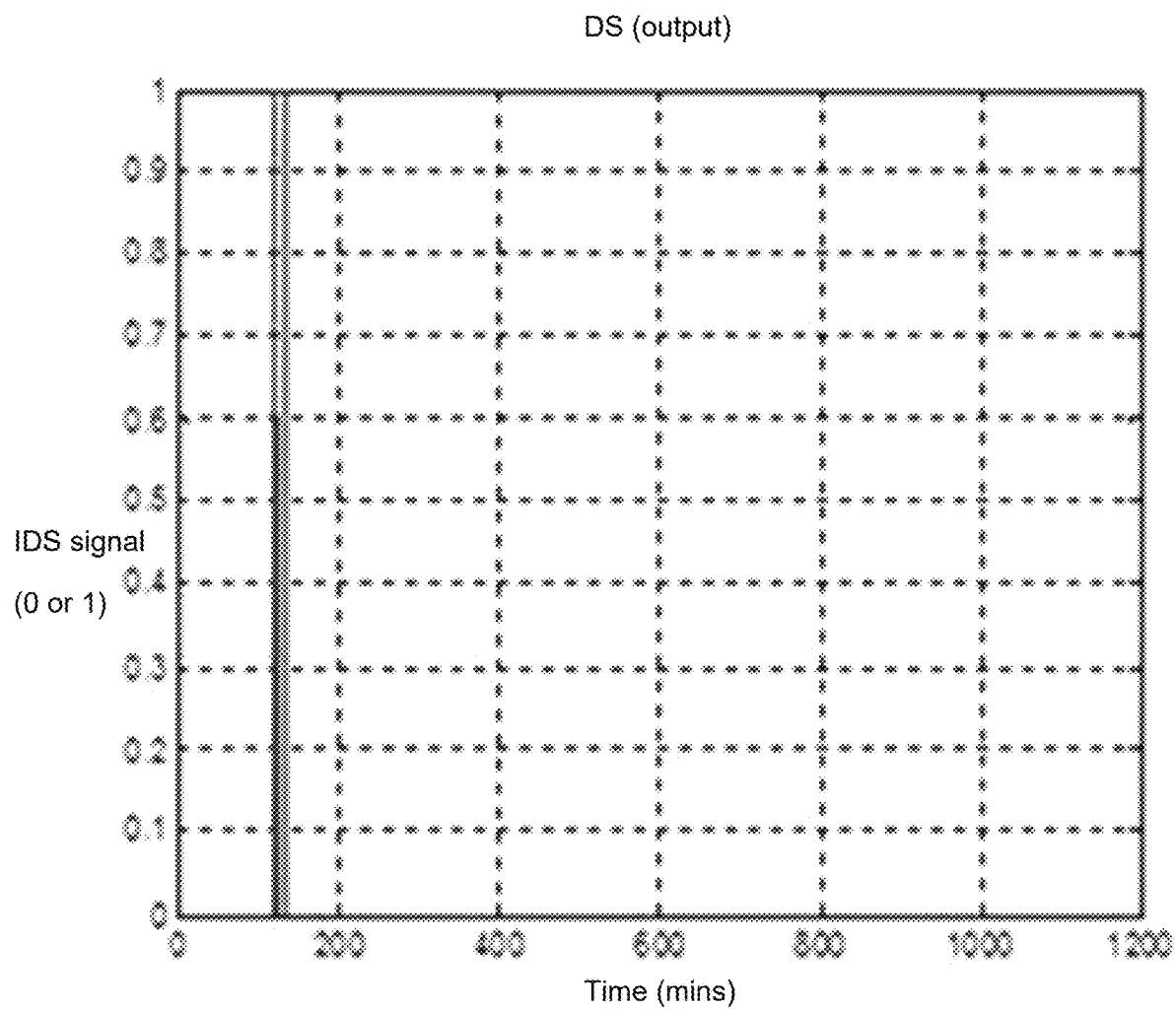
Figure 5D:
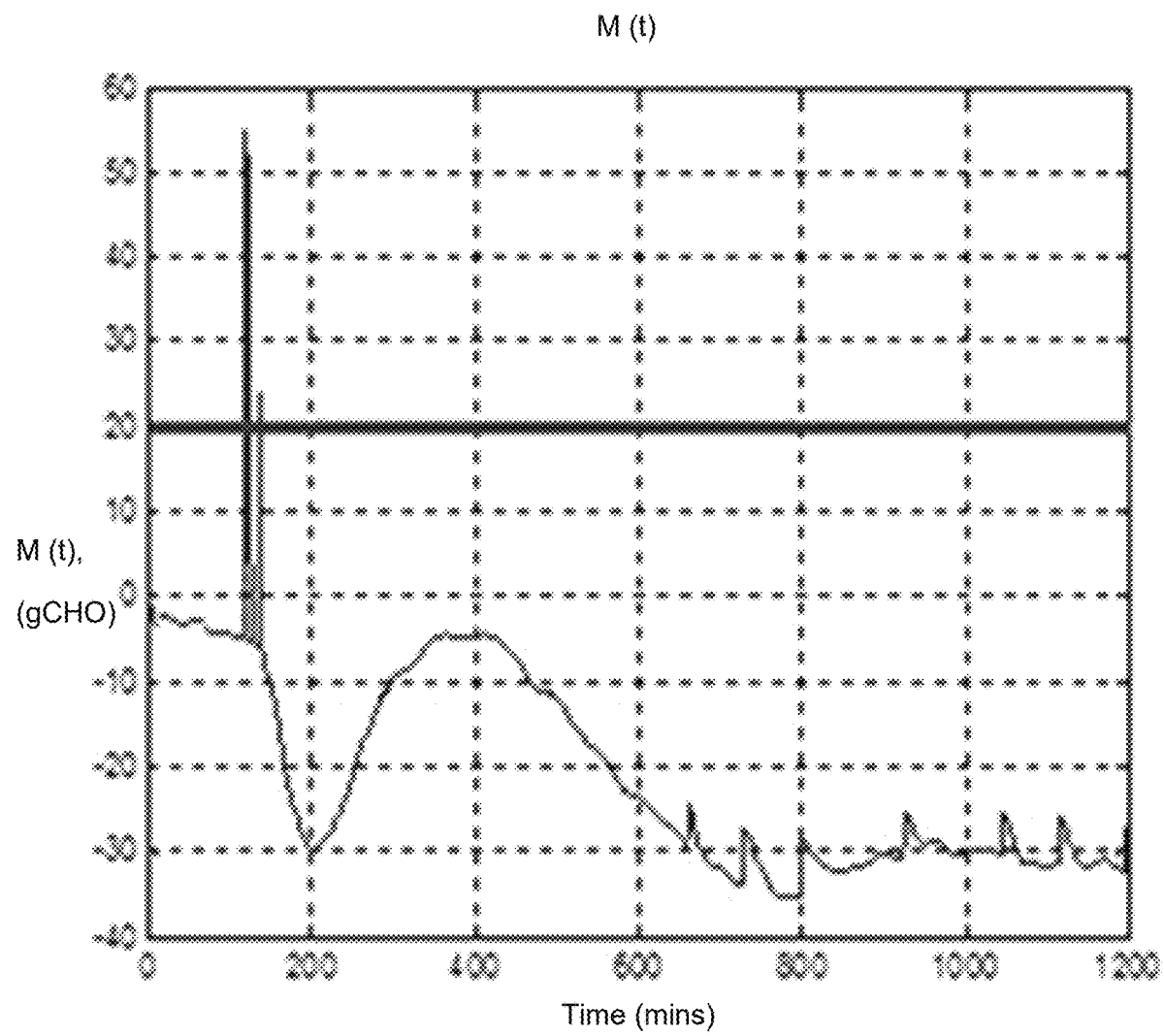
Figure 5E:
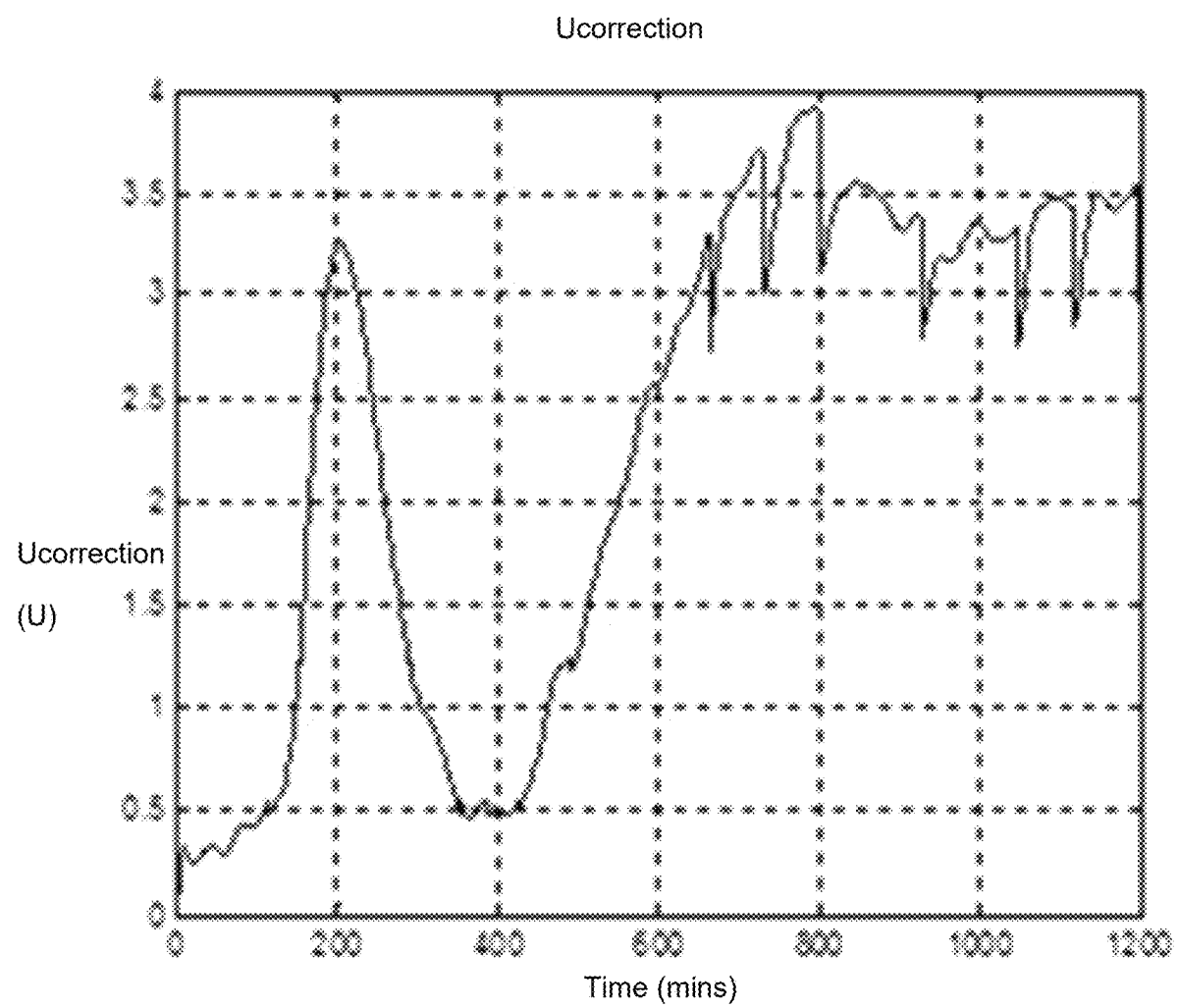

FIGS. 5A-5E show a Graphical Representation of Equations (1.13), (1.14), and (1.15) and the resulting detection signal for Method 3. FIG. 5A shows: u(t), insulin injection rate as requested by the controller. FIG. 5B shows: $BG_{proj}$ computed by Equation (1.13) with $BG_{thresh}$=120 mg/dl shown in red. FIG. 5C shows: $\hat{U}_{correction}$ computed by Equation (1.14). FIG. 5D shows: M(t) computed by Equation (1.15) with $carb_{thresh}$=20 g shown in red. FIG. 5E shows: Detection Signal: "0" indicates that the insulin request passes through the IDS undetected, while "1" indicates that the insulin request is detected by the IDS and user approval is sought.

Figure 6A:
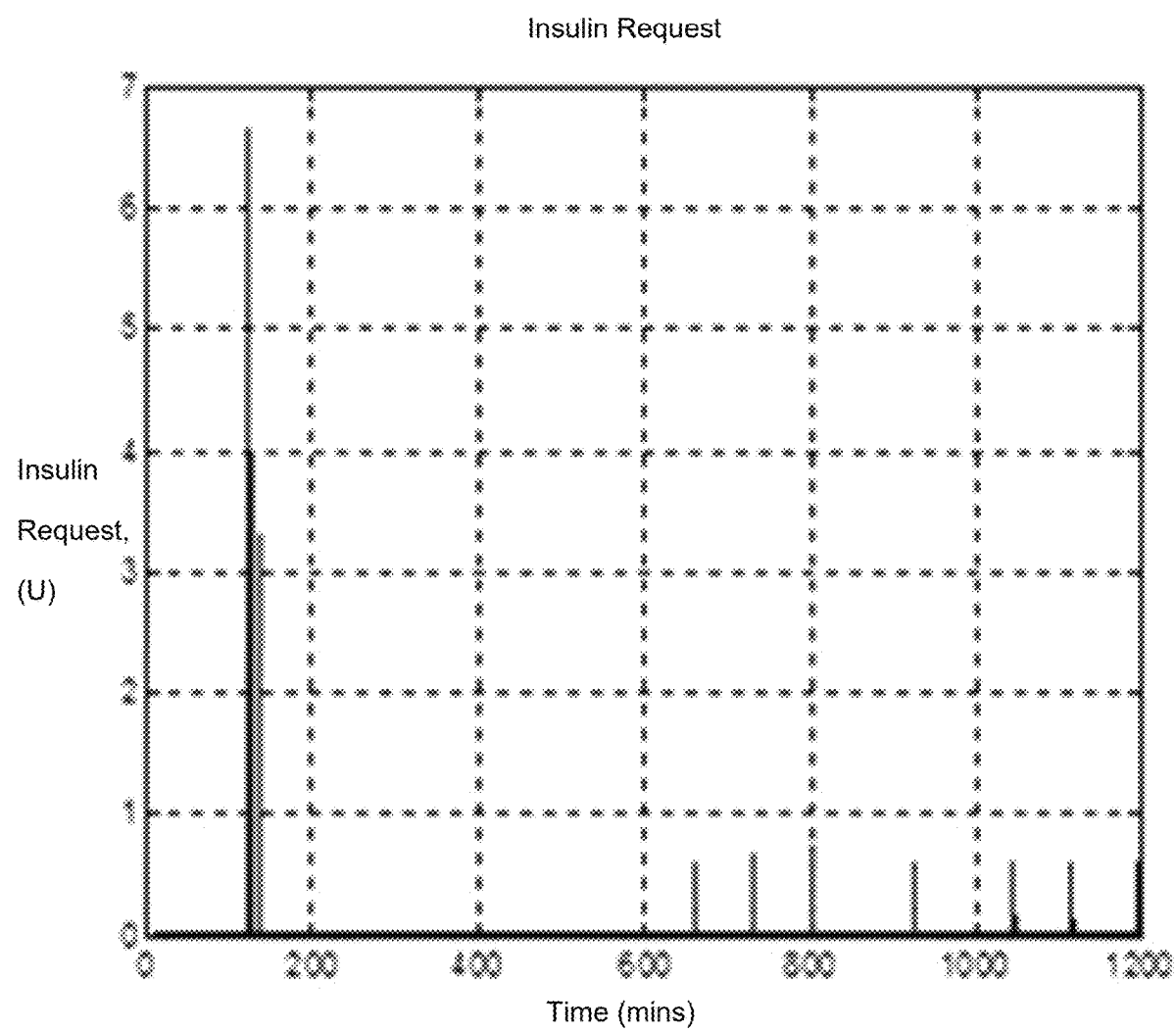
FIGS. 6A-6E show a graphical representation of equations (1.17), (1.20), and (1.21) and the resulting detection signal for Method 4.
Figure 6B:
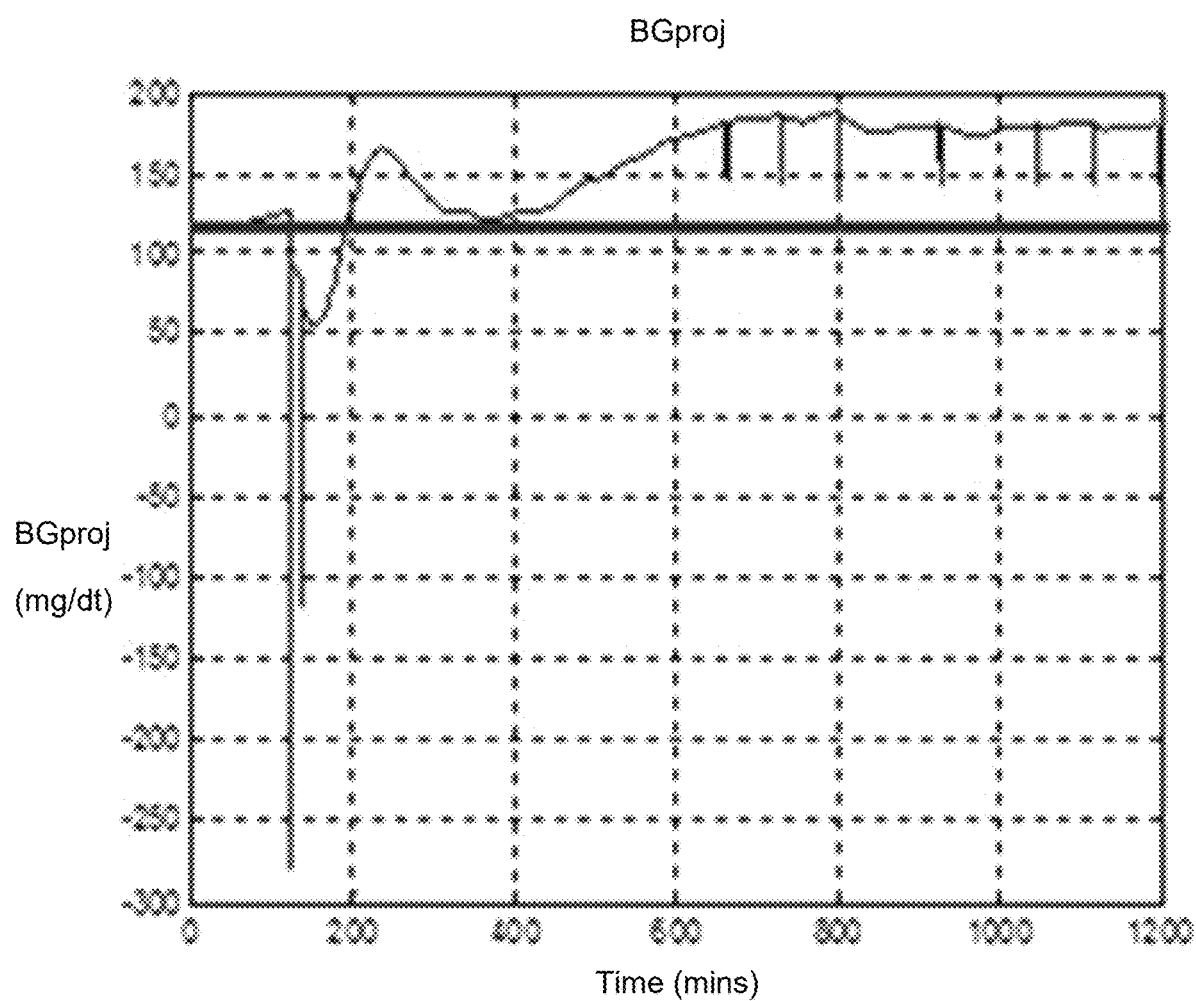
Figure 6C:
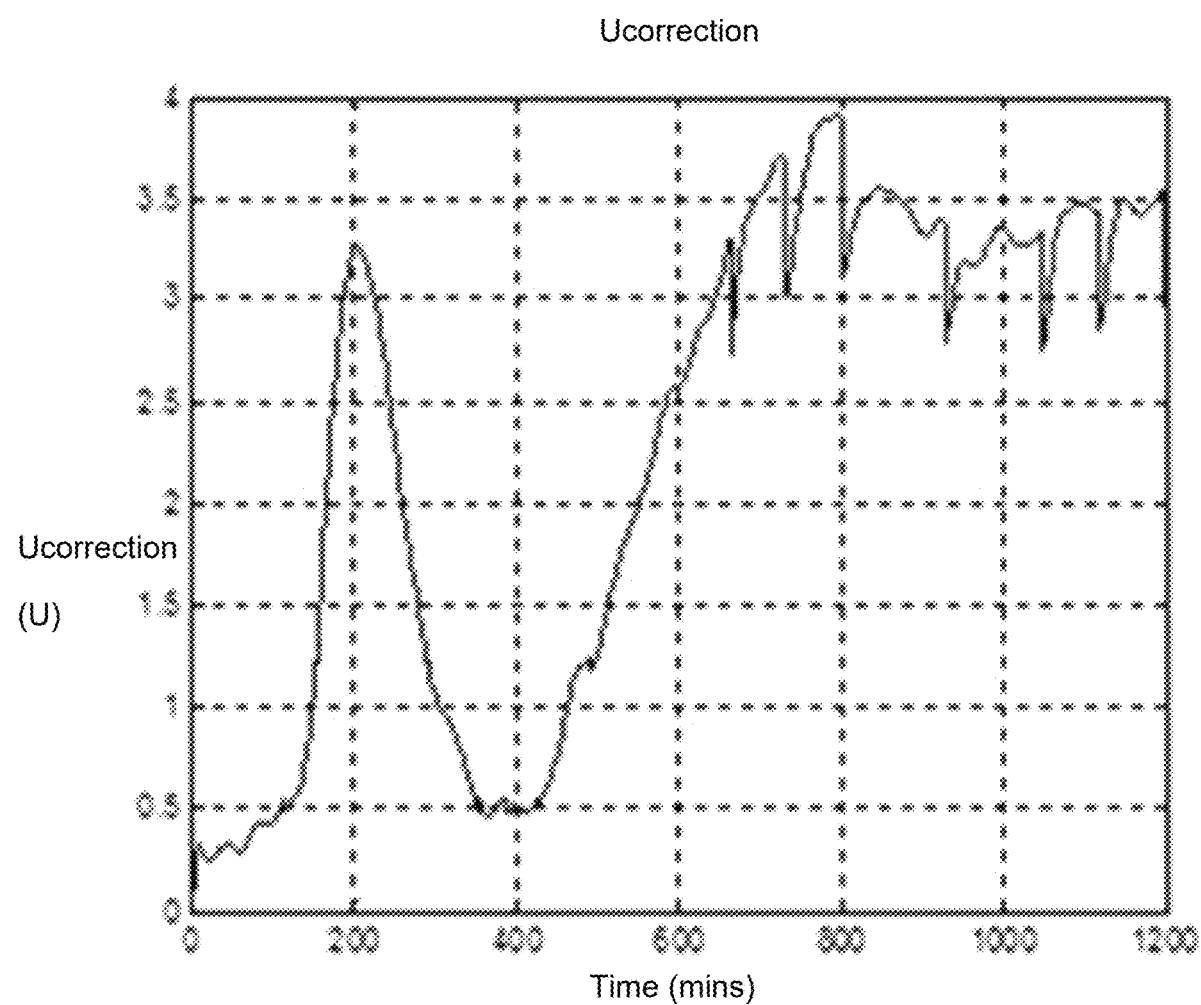
Figure 6D:
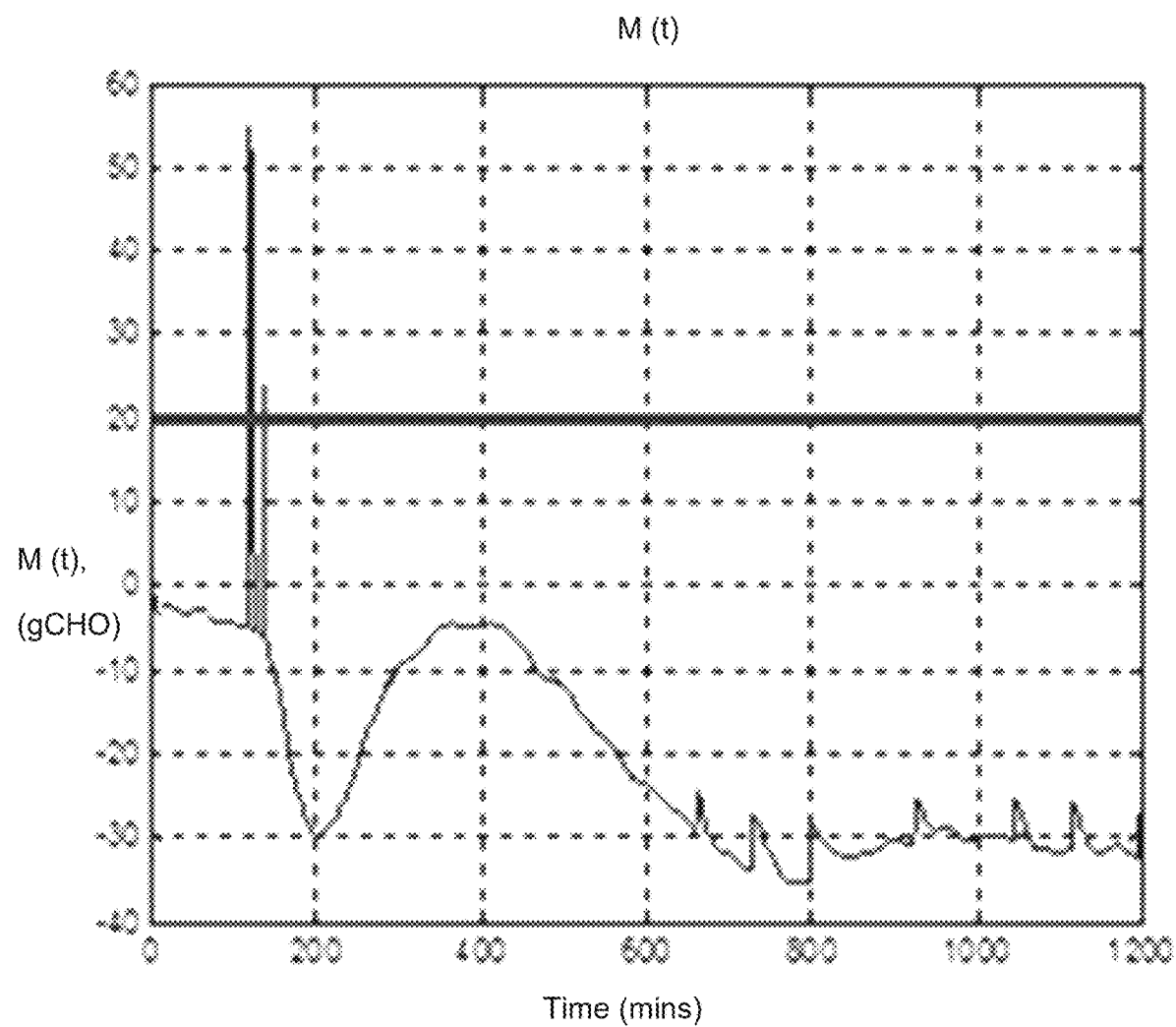
Figure 6E:
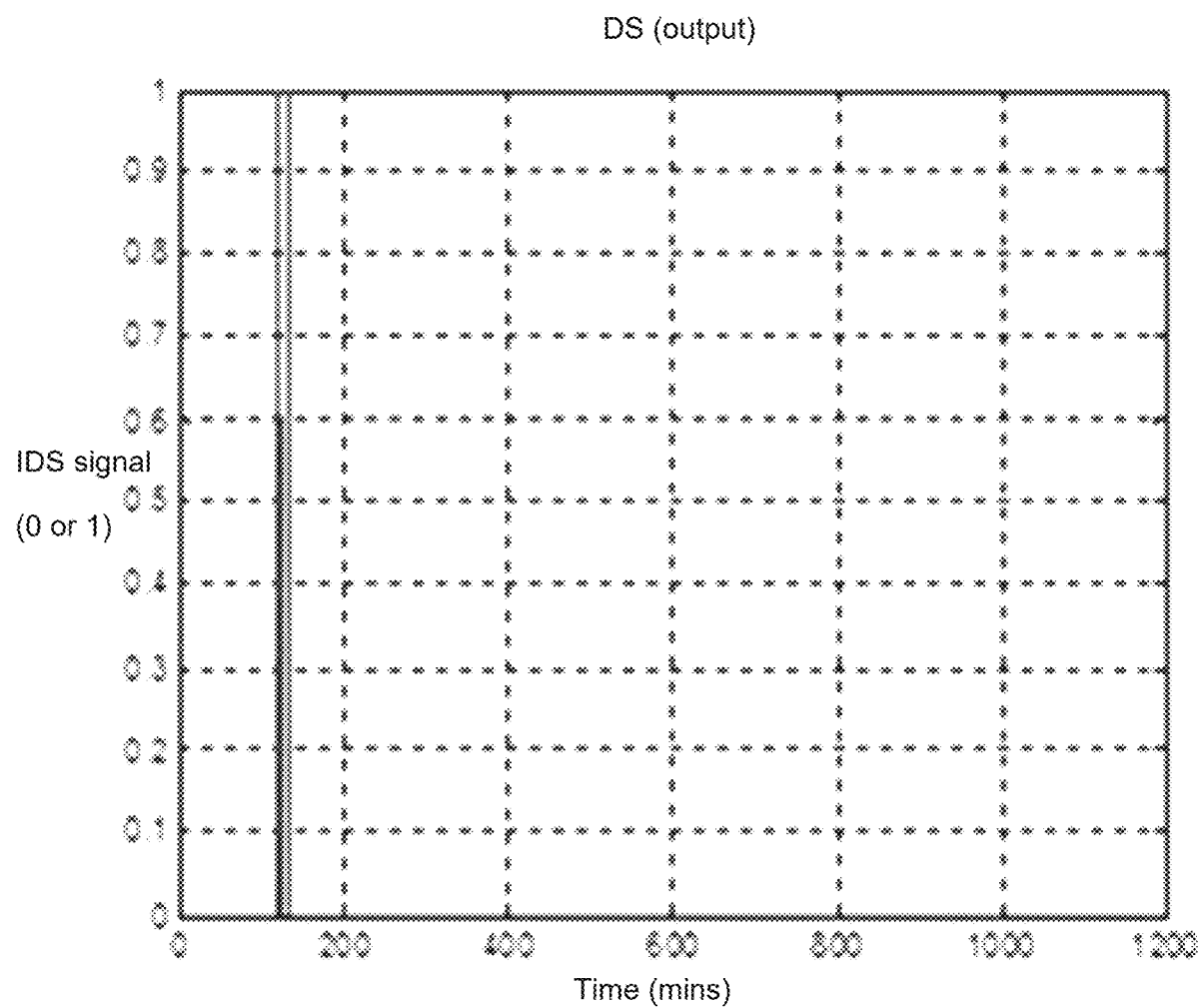

FIGS. 6A-6E show a graphical representation of equations (1.17), (1.20), and (1.21) and the resulting detection signal for Method 4. FIG. 6A shows: u(t), insulin injection rate as requested by the controller. FIG. 6B shows: $BG_{proj}$ computed by Equation (1.17) with $\tau$=45 minutes and $BG_{thresh}$=120 mg/dl shown in red. FIG. 6C shows: $\hat{U}_{correction}$ computed by Equation (1.20). FIG. 6D shows: M(t) computed by Equation (1.21) with $carb_{thresh}$=20 g shown in red. FIG. 6E shows: Detection Signal: "0" indicates that the insulin request passes through the IDS undetected, while "1" indicates that the insulin request is detected by the IDS and user approval is sought.

An aspect of an embodiment of the present invention method, system and computer program product relates to supervision of insulin delivery via insulin pump or insulin pen, which will provide for improved safety in insulin treated patients.

Using a real-time assessment of the effect of insulin requests on a patient's blood glucose level, the system will detect excessive insulin requests and request user approval of these insulin amounts before the insulin requests are sent to the insulin delivery mechanism. The detection of excessive insulin amounts is assessed using CGM or SMBG data and insulin mechanism feedback. It is anticipated that the system will be applicable, in different embodiments, to enhance existing insulin pumps and insulin pens equipped with memory and data processing capabilities.

This system and related method will dramatically increase the safety of insulin users, and will thereby allow for tighter glucose control by limiting the risk of hypoglycemia, one of the major hurdles in achieving tight glycemic control.

Aspects of various embodiments of the present invention innovates in several ways on existing technologies by, but not limited thereto, the following:

1. using insulin delivery data (from the insulin pump or other device such as insulin pen) as a primary source of information for safety analysis;
2. intercepting insulin boluses prior to their delivery and thereby improving the safety of insulin delivery in a preventative way, as opposed to correcting for errors in insulin delivery after delivery occurs (e.g. via pump shutoff techniques or glucagon injection);
3. detection of any potentially hazardous insulin amount without or with blood glucose information;
4. in particular, detecting the arrival of a pre-meal bolus prior to, or at the time of, the arrival of the meal (typically meal boluses are detected only by observation of increasing blood glucose concentrations following the meal).
5. integrating an alert system that communicates with the user to request user intervention prior to insulin being delivered, giving the user the capability to measure blood glucose (if no data is available), modify or cancel insulin amounts, be alerted of the need for carbohydrate consumption, and be advised about the amount of carbohydrate needed to avoid hypoglycemia An aspect of various embodiments of the present invention may provide a number of advantages, such as but not limited thereto, the following:

1. it uses the signal from the insulin delivery mechanism as a primary source of information for the safety analysis of insulin delivery in diabetes; this allows for preventative action against a potentially incoming hypoglycemic event as well as a more robust and earlier restoration of optimal insulin therapy;
2. it works with or without recent blood glucose readings;
3. it is applicable to both insulin pumps and insulin pens equipped with memory and data processing capabilities;
4. it allows for the interception of insulin requests prior to insulin delivery;
5. it represents a meal detector that is superior to meal-detection systems that are based solely on blood glucose readings;
6. it allows for communication with the user prior to insulin delivery in the event that insulin requests are deemed potentially hazardous, or pre-meal insulin amounts. This communication with the user allows for user action in modifying the insulin request and to alert the user that additional action should be taken if the insulin request is delivered;
7. it adapts to the patient-specific desired level of alert by individual patient parameter adjustment;

By utilizing the signal from the insulin delivery mechanism as the primary source of safety analysis, this method (and related system and computer program product) allows for an intermediary step between the insulin request and the insulin delivery where insulin requests can be assessed for their safety. By reducing risk of hypoglycemia by communicating with the user and allowing for modification of insulin requests prior to their delivery, an aspect of an embodiment of the invention will have positive impact on the life of diabetic patients and their overall health. Diabetes care is a very active industrial domain, with several major pharmaceutical companies and numerous smaller businesses proposing insulin injection system and glucose monitors. An embodiment of the present invention has the potential to reside in an insulin pump or other insulin delivery device equipped with certain data processing power (e.g. contemporary insulin pens), and can be implemented in a third party device so long as it can receive information about requested insulin prior to its delivery. This device and method can be used with either self-monitoring or continuous glucose monitoring, but does not require blood glucose information for its core function.

Figure 7:
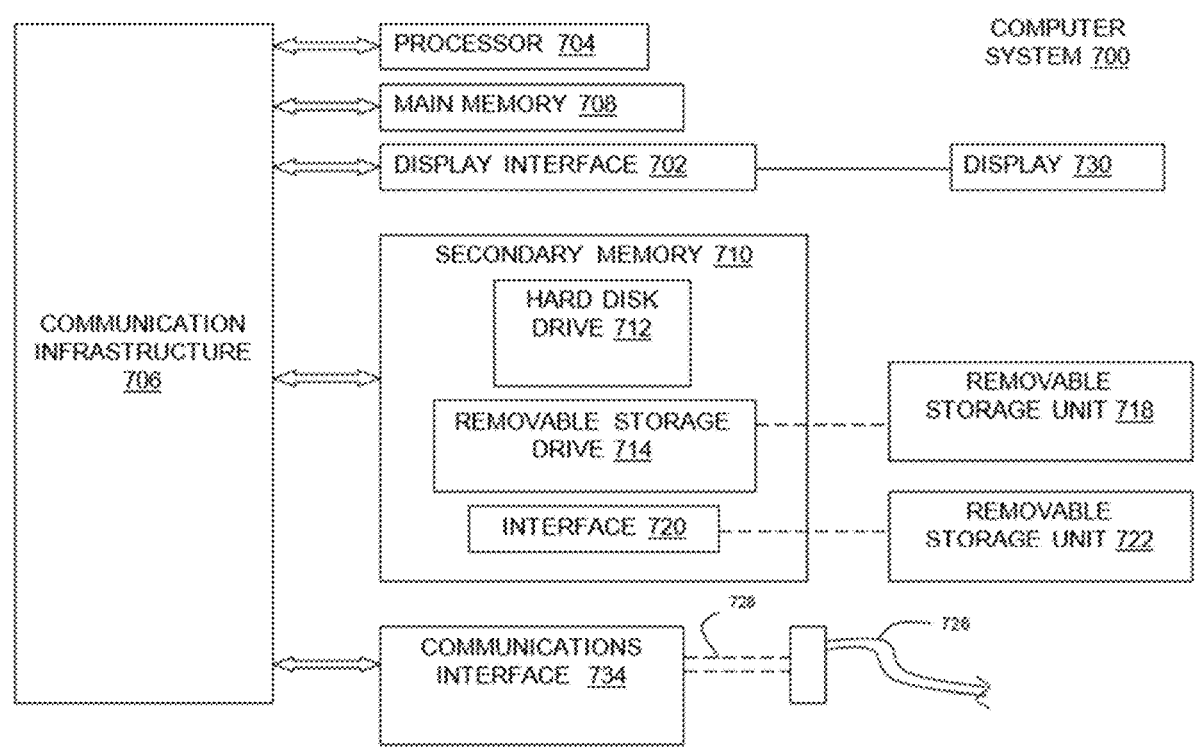
FIG. 7 shows a functional block diagram for a computer system for implementation of an exemplary embodiment or portion of an embodiment of present invention.

FIG. 7 shows a functional block diagram for a computer system 700 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 70 as illustrated in FIG. 7. The computer system 700 may includes one or more processors, such as processor 704. The Processor 704 is connected to a communication infrastructure 706 (e.g., a communications bus, cross-over bar, or network). The computer system 700 may include a display interface 702 that forwards graphics, text, and/or other data from the communication infrastructure 706 (or from a frame buffer not shown) for display on the display unit 730. Display unit 730 may be digital and/or analog.

The computer system 700 may also include a main memory 708, preferably random access memory (RAM), and may also include a secondary memory 710. The secondary memory 710 may include, for example, a hard disk drive 712 and/or a removable storage drive 714, representing a floppy disk drive, a magnetic tape drive, an optical disk drive, a flash memory, etc. The removable storage drive 714 reads from and/or writes to a removable storage unit 718 in a well known manner. Removable storage unit 718, represents a floppy disk, magnetic tape, optical disk, etc. which is read by and written to by removable storage drive 714. As will be appreciated, the removable storage unit 718 includes a computer usable storage medium having stored therein computer software and/or data.

In alternative embodiments, secondary memory 710 may include other means for allowing computer programs or other instructions to be loaded into computer system 700. Such means may include, for example, a removable storage unit 722 and an interface 720. Examples of such removable storage units/interfaces include a program cartridge and cartridge interface (such as that found in video game devices), a removable memory chip (such as a ROM, PROM, EPROM or EEPROM) and associated socket, and other removable storage units 722 and interfaces 720 which allow software and data to be transferred from the removable storage unit 722 to computer system 700.

The computer system 700 may also include a communications interface 724. Communications interface 124 allows software and data to be transferred between computer system 700 and external devices. Examples of communications interface 724 may include a modem, a network interface (such as an Ethernet card), a communications port (e.g., serial or parallel, etc.), a PCMCIA slot and card, a modem, etc. Software and data transferred via communications interface 724 are in the form of signals 728 which may be electronic, electromagnetic, optical or other signals capable of being received by communications interface 724. Signals 728 are provided to communications interface 724 via a communications path (i.e., channel) 726. Channel 726 (or any other communication means or channel disclosed herein) carries signals 728 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 714, a hard disk installed in hard disk drive 712, and signals 728. These computer program products ("computer program medium" and "computer usable medium") are means for providing software to computer system 700. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 708 and/or secondary memory 710. Computer programs may also be received via communications interface 724. Such computer programs, when executed, enable computer system 700 to perform the features of the present invention as discussed herein. In particular, the computer programs, when executed, enable processor 704 to perform the functions of the present invention. Accordingly, such computer programs represent controllers of computer system 700.

In an embodiment where the invention is implemented using software, the software may be stored in a computer program product and loaded into computer system 700 using removable storage drive 714, hard drive 712 or communications interface 724. The control logic (software or computer program logic), when executed by the processor 704, causes the processor 704 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

One embodiment of the present invention relates to a safety supervision module in open- and closed-loop control of diabetes.

Embodiments can continuously monitor patient status; reduce or discontinue insulin delivery to prevent or minimize hypoglycemia. Embodiments can act independently of the mode of insulin administration (open- or closed-loop control). Embodiments can operate within a modular architecture for control; act as intermediary between control and physical layers of the system.

Embodiments can employ Power Brakes [12], which can use CGM data to assess risk of hypoglycemia and compute reduction of insulin delivery rate. Other embodiments can employ Insulin-on-Board (IOB) Constraints, which can use insulin pump data to assess active insulin and compute limits on insulin delivery. Still other embodiments can employ an integrated system, which can allow insulin according to the minimum of the two effects above, relaxing both safety mechanisms in the time frame immediately following meals.

Figure 8:
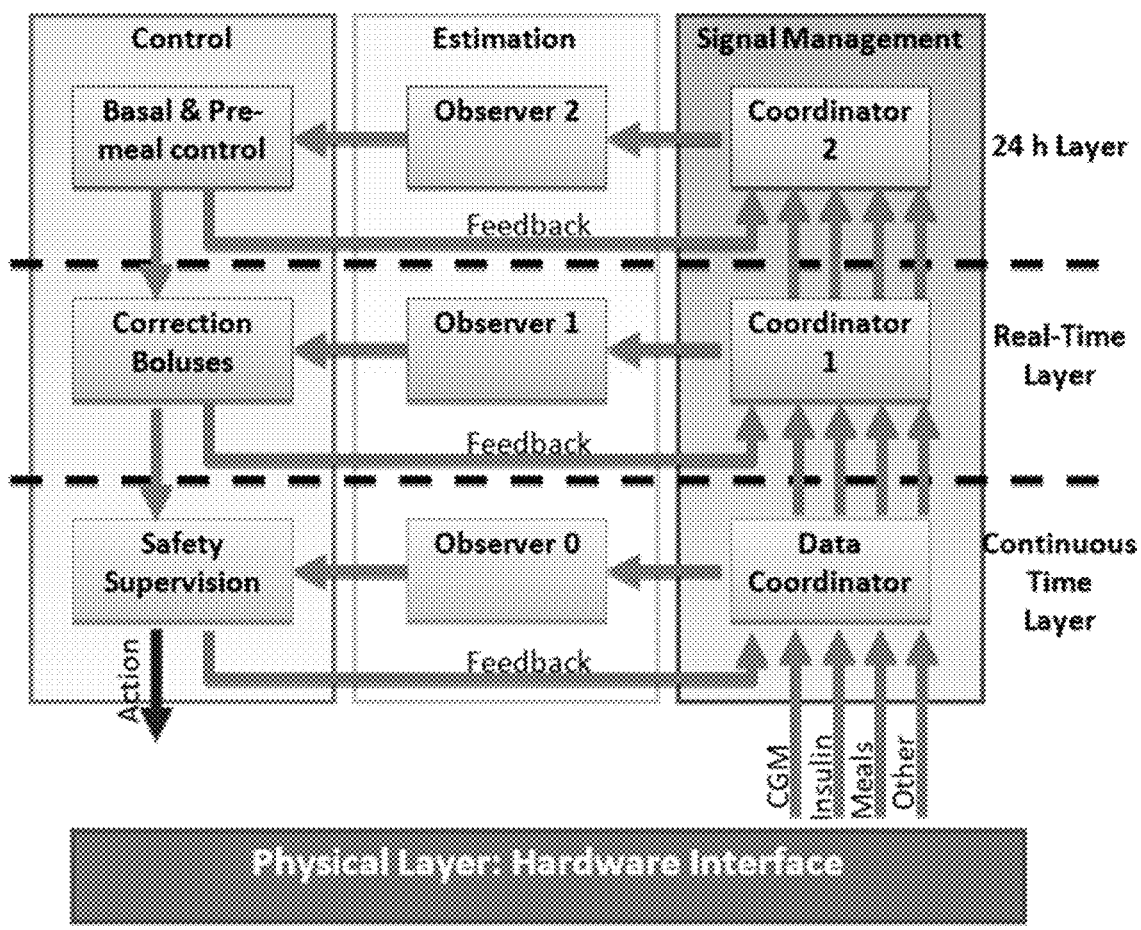
FIG. 8 shows a block diagram detailing the modular control architecture where the IDS may reside (represented by the "Safety Supervision" block of the architecture, of which the IDS is a proposed component)

FIG. 8 shows a block diagram detailing a modular control architecture [13] where the IDS can reside as part of a "Safety Supervision" system to monitor and supervise insulin delivery.

In silico evaluation of safety supervision of PID control with miscalculated patient basal rates is shown in FIGS. 9 and 10. FIGS. 9 and 10 show test result for the experiment involving 100 simulated adult subjects in 24-hour closed-loop protocol starting at 10 am, with 55 g CHO at 12 pm, 75 g at 6 pm, 50 g at 7 am.

With PID only control 2% of subjects fall below 60 mg/dl, 7% fall below 70 mg/dl with safety supervision. As shown in FIG. 9, with safety supervision according to an embodiment of the invention 0% of subjects fall below 60 mg/dl, 0% fall below 70 mg/dl.

For Miscalculated Basal Rates (1.5× nominal) frequent SSM intervention can be required. For PID only control 57% of subjects fall below 60 mg/dl, 80% fall below 70 mg/dl. As shown in FIG. 10, with safety supervision according to an embodiment of the invention 4% of subjects fall below 60 mg/dl, 7% fall below 70 mg/dl.

Based on these results, it can be concluded safety supervision is a natural component of external glucose control, and in closed-loop applications the SSM prevents hypoglycemia by independently modifying closed-loop control actions.

PUBLICATIONS

The following patents, applications and publications as listed below and throughout this document are hereby incorporated by reference in their entirety herein.
1. The Diabetes Control and Complications Trial Research Group. Hypoglycemia in the Diabetes Control and Complications Trial. Diabetes 46: 271-286, 1997
2. Henderson J N, Allen K V, Deary I J, Frier B M. Hypoglycemia in insulin-treated Type 2 diabetes: frequency, symptoms and impaired awareness. Diabet Med 20: 1016-1021, 2003
3. Cryer P E. Hypoglycaemia: The limiting factor in the glycaemic management of type I and type II diabetes. Diabetologia 45: 937-948, 2002
4. Cryer P E. Iatrogenic hypoglycemia as a cause of hypoglycemia-associated autonomic failure in IDDM: A vicious cycle. Diabetes 41:255-260, 1992
5. Gold A E, Deary I J, Frier B M. Recurrent severe hypoglycaemia and cognitive function in type I diabetes. Diabet Med 10:503-508, 1993
6. Segel S A, Paramore D S, Cryer P E. Hypoglycemia-associated autonomic failure in advanced type 2 diabetes. Diabetes 51: 724-733, 2002
7. G. McGarraugh and R. Bergenstal, "Detection of hypoglycemia with continuous interstitial and traditional blood glucose monitoring using the FreeStyle Navigator Continuous Glucose Monitoring System," Diabetes Technology and Therapeutics, vol. 11(3), pp. 145-150, 2009.
8. S. E. Noujaim, D. Horwitz, M. Sharma, J. Marhoul, "Accuracy requirements for a hypoglycemia detector: an analytical model to evaluate the effects of bias, precision, and rate of glucose change," Journal of Diabetes Science and Technology, vol. 1(5), pp. 653-668, 2007.
9. W. K. Ward, "The role of new technology in the early detection of hypoglycemia," Diabetes Technology and Therapeutics, vol. 6(2), pp. 115-117, 2004.
10. B. Buckingham, E. Cobry, P. Clinton, V. Gage, K. Caswell, E. Kunselman, F. Cameron, and H. P. Chase, "Preventing hypoglycemia using predictive alarm algorithms and insulin pump suspension," Diabetes Technology and Therapeutics, vol. 11(2), pp. 93-97, 2009.
11. J Walsh, R. Roberts. Pumping Insulin: Everything You Need For Success On A Smart Insulin Pump. 4th ed. 2006.
12. Hughes, C S, Patek, S D, Breton, M, Kovatchev, B P. Hypoglycemia Prevention via Pump Attenuation and Red-Yellow-Green "Traffic" Lights using CGM and Insulin Pump Data. Journal of Diabetes Science and Technology. 2010; 1146-1155.
13. B. Kovatchev, S. Patek, E. Dassau, F. J. Doyle III, L. Magni, G. De Nicalao, C. Cobelli. Control to Range for Diabetes: Functionality and Modular Architecture. Journal of Diabetes Science and Technology. 3(5). 2009; 1058-1065.

The devices, systems, and computer program products, and methods of various embodiments of the invention disclosed herein may utilize aspects disclosed in the following references, applications, publications and patents and which are hereby incorporated by reference herein in their entirety:
1A. International Patent Application Serial No. PCT/US2010/025405, entitled "Method, System and Computer Program Product for CGM-Based Prevention of Hypoglycemia via Hypoglycemia Risk Assessment and Smooth Reduction Insulin Delivery," filed Feb. 25, 2010
1. 1B. PCT/US2008/082063, entitled "Model Predictive Control Based Method for Closed-Loop Control of Insulin Delivery in Diabetes Using Continuous Glucose Sensing", filed Oct. 31, 2008.
2. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008.
3. PCT/US2008/067725, entitled "Method, System and Computer Simulation Environment for Testing of Monitoring and Control Strategies in Diabetes," filed Jun. 20, 2008.
4. PCT/US2008/067723, entitled "LQG Artificial Pancreas Control System and Related Method", filed on Jun. 20, 2008.
5. U.S. Ser. No. 12/516,044, filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes;"
6. PCT/US2007/085588 not yet published filed Nov. 27, 2007, entitled "M eth od, System, and Computer Program Product for the Detection of Physical Activity by Changes in Heart Rate, Assessment of Fast Changing Metabolic States, and Applications of Closed and Open Control Loop in Diabetes;"
7. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes;"
8. U.S. patent application Ser. No. 11/578,831, filed Oct. 18, 2006 entitled "Method, System and Computer Program Product for Evaluating the Accuracy of Blood Glucose Monitoring Sensors/Devices".
9. PCT International Application Serial No. PCT/US2005/013792, filed Apr. 21, 2005, entitled "Method, System, and Computer Program Product for Evaluation of the Accuracy of Blood Glucose Monitoring Sensors/Devices;"

10. PCT International Application Serial No. PCT/US01/09884, filed Mar. 29, 2001, entitled "Method, System, and Computer Program Product for Evaluation of Glycemic Control in Diabetes Self-Monitoring Data;"
11. U.S. Pat. No. 7,025,425 B2 issued Apr. 11, 2006, entitled "Method, System, and Computer Program Product for the Evaluation of Glycemic Control in Diabetes from Self-Monitoring Data;"
12. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);
13. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"
14. U.S. patent application Ser. No. 10/524,094 filed Feb. 9, 2005 entitled "Managing and Processing Self-Monitoring Blood Glucose" (Publication No. 2005/214892);
15. U.S. Ser. No. 12/065,257, filed Aug. 29, 2008, entitled "Accuracy of Continuous Glucose Sensors;"
16. PCT International Application Serial No PCT/US2006/033724, filed Aug. 29, 2006, entitled "Method for Improvising Accuracy of Continuous Glucose Sensors and a Continuous Glucose Sensor Using the Same;"
17. U.S. Ser. No. 12/159,891, filed Jul. 2, 2008, entitled "Method, System and Computer Program Product for Evaluation of Blood Glucose Variability in Diabetes from Self-Monitoring Data;"
18. PCT International Application No. PCT/US2007/000370, filed Jan. 5, 2007, entitled "Method, System and Computer Program Product for Evaluation of Blood Glucose Variability in Diabetes from Self-Monitoring Data;"
19. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors;"
20. U.S. Ser. No. 10/069,674, filed Feb. 22, 2002, entitled "Method and Apparatus for Predicting the Risk of Hypoglycemia;"
21. PCT International Application No. PCT/US00/22886, filed Aug. 21, 2000, entitled "Method and Apparatus for Predicting the Risk of Hypoglycemia;"
22. U.S. Pat. No. 6,923,763 B1, issued Aug. 2, 2005, entitled "Method and Apparatus for Predicting the Risk of Hypoglycemia;" and
23. Kovatchev B P, Straume M, Cox D J, Farhy L S. Risk analysis of blood glucose data: A quantitative approach to optimizing the control of insulin dependent diabetes. J of Theoretical Medicine, 3:1-10, 2001.

What is claimed is:

1. A method for detecting and correcting for an excessive insulin request, the method comprising:
intercepting a signal requesting delivery to a patient of an amount of insulin at time t, u(t), wherein u(t) is based on a target blood glucose concentration, the intercepting occurring prior to the signal being received by an insulin delivery device;
determining that delivery of u(t) to the patient will result in hypoglycemia in the patient, the determining involving:
when self-monitoring BG assessment (SMBG) at time t, SMBG(t), is available:
calculating a projected blood glucose concentration of the patient based on SMBG(t);
calculating an amount of carbohydrates that is required to maintain the target blood glucose concentration for u(t); and
classifying the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold:
when SMBG(t) is not available:
estimating an amount of carbohydrates that is required to maintain the target blood glucose concentration for u(t):
classifying the insulin delivery request signal as an excessive insulin request when the estimated amount of carbohydrates that is required to maintain the target blood glucose concentration for u(t) is greater than a carbohydrate amount threshold:
requesting SMBG(t) when the insulin delivery request signal is classified as an excessive insulin request:
upon receiving the SMBG(t):
calculating a projected blood glucose concentration of the patient based on SMBG(t);
calculating an amount of carbohydrates that is required to maintain the target blood glucose concentration for u(t); and
classifying the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold;
when the insulin delivery request signal is classified as an excessive insulin request, generating an updated u(t) based on a blood glucose concentration threshold as opposed to the target blood glucose concentration for u(t); and
transmitting the updated u(t) to the insulin delivery device.

2. The method of claim 1, wherein SMBG(t) is not available includes a SMBG not being available during any time prior to and including time t.

3. The method of claim 1, wherein when SMBG(t) is available:
generating an instruction to consume the calculated amount of carbohydrates that is required to maintain the target blood glucose concentration for u(t).

4. The method of claim 3, comprising:
receiving a signal that the calculated amount of carbohydrates that is required to maintain the target blood glucose concentration for u(t) has been consumed.

5. The method of claim 4, comprising:
transmitting the un-updated u(t), as opposed to the updated u(t), to the insulin delivery device.

6. The method of claim 1, wherein when SMBG(t) is not available:
generating an instruction to consume the estimated amount of carbohydrates that is required to maintain the target blood glucose concentration for u(t).

7. The method of claim 6, comprising:
receiving a signal that the estimated amount of carbohydrates that is required to maintain the target blood glucose concentration for u(t) has been consumed.

8. The method of claim 7, comprising:
transmitting the un-updated u(t), as opposed to the updated u(t), to the insulin delivery device for delivery of insulin to the patient.

9. A system for detecting and correcting for an excessive insulin request, comprising:
an insulin delivery device configured to deliver an amount of insulin to a diabetic patient in response to a request signal; and
a safety supervision module configured for:
intercepting a signal requesting delivery to the patient of an amount of insulin at time t, u(t), wherein u(t) is based on a target blood glucose concentration, the intercepting occurring prior to the signal being received by the insulin delivery device;
determining that delivery of u(t) to the patient will result in hypoglycemia in the patient, the determining involving:
when self-monitoring BG assessment (SMBG) at time t, SMBG(t), is available:
calculating a projected blood glucose concentration of the patient based on SMBG(t);
calculating an amount of carbohydrates that is required to maintain the target blood glucose concentration for u(t); and
classifying the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold;
when SMBG(t) is not available:
estimating an amount of carbohydrates that is required to maintain the target blood glucose concentration for u(t):
classifying the insulin delivery request signal as an excessive insulin request when the estimated amount of carbohydrates that is required to maintain the target blood glucose concentration for u(t) is greater than a carbohydrate amount threshold:
requesting SMBG(t) when the insulin delivery request signal is classified as an excessive insulin request:
upon receiving the SMBG(t):
calculating a projected blood glucose concentration of the patient based on SMBG(t);
calculating an amount of carbohydrates that is required to maintain the target blood glucose concentration for u(t); and
classifying the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold:
when the insulin delivery request signal is classified as an excessive insulin request, generating an updated u(t) based on a blood glucose concentration threshold as opposed to the target blood glucose concentration for u(t); and
transmitting the updated u(t) to the insulin delivery device.

10. The system of claim 9, wherein SMBG(t) is not available includes a SMBG not being available during any time prior to and including time t.

11. The system of claim 9, wherein when SMBG(t) is available the safety supervision module is configured for:
generating an instruction to consume the calculated amount of carbohydrates that is required to maintain the target blood glucose concentration for u(t).

12. The system of claim 11, wherein the safety supervision module is configured for:
receiving a signal that the calculated amount of carbohydrates that is required to maintain the target blood glucose concentration for u(t) has been consumed.

13. The system of claim 12, wherein the safety supervision module is configured for:
transmitting the un-updated u(t), as opposed to the updated u(t), to the insulin delivery device.

14. The system of claim 9, wherein when SMBG(t) is not available the safety supervision module is configured for:
generating an instruction to consume the estimated amount of carbohydrates that is required to maintain the target blood glucose concentration for u(t).

15. The system of claim 14, wherein the safety supervision module is configured for:
receiving a signal that the estimated amount of carbohydrates that is required to maintain the target blood glucose concentration for u(t) has been consumed.

16. The system of claim 15, wherein the safety supervision module is configured for:
transmitting the un-updated u(t), as opposed to the updated u(t), to the insulin delivery device.

17. A non-transitory computer readable medium having stored thereon computer executable instructions for detecting and correcting for an excessive insulin request that when executed cause at least one processor to:
intercept a signal requesting delivery to a patient of an amount of insulin at time t, u(t), wherein u(t) is based on a target blood glucose concentration, the intercepting occurring prior to the signal being received by an insulin delivery device;
determine that delivery of u(t) to the patient will result in hypoglycemia in the patient, the determining involving:
when self-monitoring BG assessment (SMBG) at time t, SMBG(t), is available:
calculate a projected blood glucose concentration of the patient based on SMBG(t);
calculate an amount of carbohydrates that is required to maintain the target blood glucose concentration for u(t); and
classify the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold;
when SMBG(t) is not available:
estimate an amount of carbohydrates that is required to maintain the target blood glucose concentration for u(t):

classify the insulin delivery request signal as an excessive insulin request when the estimated amount of carbohydrates that is required to maintain the target blood glucose concentration for u(t) is greater than a carbohydrate amount threshold;

request SMBG(t) when the insulin delivery request signal is classified as an excessive insulin request:

upon receiving the SMBG(t):
    calculate a projected blood glucose concentration of the patient based on SMBG(t):
    calculate an amount of carbohydrates that is required to maintain the target blood glucose concentration for u(t); and
    classify the insulin delivery request signal as an excessive insulin request when the calculated projected blood glucose concentration is less than a blood glucose concentration threshold and when the calculated amount of carbohydrates that is required to maintain the target blood glucose concentration for u(t) is greater than a carbohydrate amount threshold:

when the insulin delivery request signal is classified as an excessive insulin request, generate an updated u(t) based on a blood glucose concentration threshold as opposed to the target blood glucose concentration for u(t); and transmit the updated u(t) to the insulin delivery device.

18. The non-transitory computer readable medium of claim 17, wherein SMBG(t) is not available includes a SMBG not being available during any time prior to and including time t.

19. The non-transitory computer readable medium of claim 17, wherein when SMBG(t) is available the at least one processor:

generates an instruction to consume the calculated amount of carbohydrates that is required to maintain the target blood glucose concentration for u(t).

20. The non-transitory computer readable medium of claim 17, wherein when SMBG(t) is not available the at least one processor:

generates an instruction to consume the estimated amount of carbohydrates that is required to maintain the target blood glucose concentration for u(t).

* * * * *